(12) United States Patent
Hohl et al.

(10) Patent No.: US 12,053,279 B2
(45) Date of Patent: Aug. 6, 2024

(54) NEAR-FIELD COMMUNICATION SECURITY FOR MEDICAL DEVICE AND SHEATH

(71) Applicant: ViOptix, Inc., Newark, CA (US)

(72) Inventors: David Keith Hohl, Milpitas, CA (US); Richard Matthew Wiard, Campbell, CA (US); Sarah Yi Wang, Monterey, CA (US)

(73) Assignee: ViOptix, Inc., Newark, CA (US)

( * ) Notice: Subject to any disclaimer, the term of this patent is extended or adjusted under 35 U.S.C. 154(b) by 467 days.

(21) Appl. No.: 17/146,176

(22) Filed: Jan. 11, 2021

(65) Prior Publication Data

US 2021/0212612 A1 Jul. 15, 2021

Related U.S. Application Data

(60) Provisional application No. 62/959,757, filed on Jan. 10, 2020.

(51) Int. Cl.
*A61B 5/145* (2006.01)
*A61B 5/00* (2006.01)
(Continued)

(52) U.S. Cl.
CPC .......... *A61B 5/14551* (2013.01); *A61B 5/002* (2013.01); *A61B 5/0022* (2013.01);
(Continued)

(58) Field of Classification Search
CPC ... A61B 5/14551; A61B 5/002; A61B 5/0022; A61B 2503/10; A61B 2503/40;
(Continued)

(56) References Cited

U.S. PATENT DOCUMENTS 5,517,301 A 5/1996 Dave
6,516,209 B2 2/2003 Cheng et al.
(Continued)

FOREIGN PATENT DOCUMENTS

WO 200212854 A2 2/2002
WO 2011008382 A1 1/2011
(Continued)

OTHER PUBLICATIONS

Heikenfeld, "Wearable sensors: modalities, challenges, and prospects",2018, Royal Society of Chemistry, pp. 217-248 (Year: 2018).*
(Continued)

*Primary Examiner* — Piotr Poltorak
*Assistant Examiner* — Gregory A Lane
(74) *Attorney, Agent, or Firm* — Aka Chan LLP

(57) ABSTRACT

A device includes a bottom housing that includes a printed circuit board, a processor formed on the printed circuit board, a probe tip coupled to the processor, and a first wall. The first wall includes a front side surface, a backside surface, and an opening extending from the front side surface to the backside surface. The printed circuit board is coupled to the front side surface of the first wall. The printed circuit board includes a plurality of electrical contacts located on the back surface and coupled to the processor. The electrical contacts on the backside surface of the printed circuit board are visible through the opening formed in the first wall of the bottom housing. The electrical contacts are sealed from fluid penetration and can connect to the electrical contacts of a battery connected to the device.

25 Claims, 18 Drawing Sheets

(51) Int. Cl.
  *A61B 5/1455* (2006.01)
  *G06K 7/10* (2006.01)
  *G16H 40/63* (2018.01)
  *H04W 12/037* (2021.01)
  *H04W 12/06* (2021.01)

(52) U.S. Cl.
  CPC .......... *A61B 5/742* (2013.01); *G06K 7/10297* (2013.01); *G16H 40/63* (2018.01); *H04W 12/037* (2021.01); *H04W 12/06* (2013.01); *A61B 2503/10* (2013.01); *A61B 2503/40* (2013.01); *A61B 2560/0214* (2013.01); *A61B 2562/166* (2013.01)

(58) Field of Classification Search
  CPC ...... A61B 2560/0214; A61B 2562/166; G16H 40/63; H04W 12/037; H04W 12/06; G06K 7/10297
  USPC ......................................................... 713/168
  See application file for complete search history.

(56) References Cited

U.S. PATENT DOCUMENTS

| | | | |
|---|---|---|---|
| 8,233,955 B2 | 7/2012 | Al-ali et al. | |
| 8,750,954 B2 | 6/2014 | Petersen et al. | |
| 8,798,700 B1 | 8/2014 | Heaton, II et al. | |
| 9,398,870 B2 | 7/2016 | Bechtel et al. | |
| 10,722,156 B2 | 7/2020 | Lonsinger et al. | |
| 11,375,371 B1* | 6/2022 | Carroll | H04L 63/04 |
| 2003/0105961 A1* | 6/2003 | Zatloukal | H04L 9/0825 |
| | | | 713/170 |
| 2004/0203683 A1* | 10/2004 | Engstrom | H04M 1/7246 |
| | | | 455/418 |
| 2006/0039139 A1 | 2/2006 | Maglica et al. | |
| 2007/0174472 A1* | 7/2007 | Kulakowski | H04L 63/1466 |
| | | | 709/229 |
| 2008/0015424 A1 | 1/2008 | Bernreuter | |
| 2008/0319290 A1 | 12/2008 | Mao et al. | |
| 2009/0018405 A1 | 1/2009 | Katsumura et al. | |
| 2011/0205535 A1 | 8/2011 | Soller et al. | |
| 2014/0266939 A1* | 9/2014 | Baringer | H01Q 7/00 |
| | | | 343/729 |
| 2015/0134552 A1* | 5/2015 | Engels | G06Q 10/087 |
| | | | 705/318 |
| 2016/0199028 A1 | 7/2016 | Jeon et al. | |
| 2018/0110450 A1* | 4/2018 | Lamego | A61B 5/0022 |
| 2018/0168493 A1 | 6/2018 | Bechtel et al. | |
| 2020/0196877 A1* | 6/2020 | Vo | A61B 5/6826 |
| 2020/0219628 A1* | 7/2020 | Shaya | H04W 12/50 |
| 2020/0402625 A1* | 12/2020 | Aravamudan | G06F 21/6245 |
| 2021/0133313 A1* | 5/2021 | Sakib | G06F 21/64 |

FOREIGN PATENT DOCUMENTS

| | | |
|---|---|---|
| WO | 2012100090 A2 | 7/2012 |
| WO | 2018017501 A1 | 1/2018 |
| WO | 2019051007 A1 | 3/2019 |

OTHER PUBLICATIONS

Heikenfeld, "Wearable sensors: modalities, challenges, and prospects", Nov. 28, 2017, Royal Society of Chemistry, pp. 217-243 (Year: 2017).*

International Search Report, PCT Application PCT/US2021/012995, May 20, 2021, 5 pages.

* cited by examiner

NEAR-FIELD COMMUNICATION SECURITY FOR MEDICAL DEVICE AND SHEATH

CROSS-REFERENCE TO RELATED APPLICATIONS

This application claims the benefit of U.S. patent application 62/959,757, filed Jan. 10, 2020. This application is incorporated by reference along with all other references cited in these applications.

BACKGROUND OF THE INVENTION

The present invention relates generally to optical systems that monitor parameters related to oxygen levels in tissue. More specifically, the present invention relates to optical probes, such as compact, handheld oximeters, and sheaths for the optical probes that shield the optical probes from contaminants during use and communicate status information to the optical probes regarding contaminant protection so that the optical probes are reusable.

A device includes a bottom housing that includes a printed circuit board, a processor formed on the printed circuit board, a probe tip coupled to the processor, and a first wall. The first wall includes a front side surface, a backside surface, and an opening extending from the front side surface to the backside surface. The printed circuit board is coupled to the front side surface of the first wall. The printed circuit board includes a plurality of electrical contacts located on the back surface and coupled to the processor. The electrical contacts on the backside surface of the printed circuit board are visible through the opening formed in the first wall of the bottom housing. The electrical contacts are sealed from fluid penetration and can connect to the electrical contacts of a battery connected to the device. The printed circuit board can also include a near field communication device to communicate with a sheath in which the device is located for use. The near field communication device can retrieve information from a near field communication device of the sheath to verify that the sheath is authentic.

Oximeters are medical devices used to measure the oxygen saturation of tissue in humans and living things for various purposes. For example, oximeters are used for medical and diagnostic purposes in hospitals and other medical facilities (e.g., operating rooms for surgery, recovery room for patient monitoring, or ambulance or other mobile monitoring for, e.g., hypoxia); sports and athletic purposes at a sports arena (e.g., professional athlete monitoring); personal or at-home monitoring of individuals (e.g., general health monitoring, or person training for a marathon); and veterinary purposes (e.g., animal monitoring).

In particular, assessing a patient's oxygen saturation, at both the regional and local level, is important as it is an indicator of the state of the patient's health. Thus, oximeters are often used in clinical settings, such as during surgery and recovery, where it can be suspected that the patient's tissue oxygenation state is unstable. For example, during surgery, oximeters should be able to quickly deliver accurate oxygen saturation measurements under a variety of non-ideal conditions.

Pulse oximeters and tissue oximeters are two types of oximeters that operate on different principles. A pulse oximeter requires a pulse in order to function. A pulse oximeter typically measures the absorbance of light due to pulsing arterial blood. In contrast, a tissue oximeter does not require a pulse in order to function, and can be used to make oxygen saturation measurements of a tissue flap that has been disconnected from a blood supply. Tissue oximeters can measure oxygen levels in human tissue by exploiting these light-absorption differences.

Human tissue, as an example, includes a variety of light-absorbing molecules. Such chromophores include oxygenated hemoglobin, deoxygenated hemoglobin, melanin, water, lipid, and cytochrome. Oxygenated and deoxygenated hemoglobins are generally the dominant chromophores in tissue for much of the visible and near-infrared spectral range. Light absorption differs significantly for oxygenated and deoxygenated hemoglobins at certain wavelengths of light.

Despite the success of existing oximeters, there is a continuing desire to improve oximeters by, for example, improving the reuse of oximeters; reducing or eliminating contamination during use; improving remote communication; improving measurement accuracy; reducing measurement time; lowering cost through reuse; reducing size, weight, or form factor; reducing power consumption; and for other reasons, and any combination of these.

Therefore, there is a need for improved tissue oximetry devices and methods of shielding oximetry devices during use for reuse of the devices.

BRIEF SUMMARY OF THE INVENTION

Embodiments relate to compact, handheld oximeters and sheaths that house and shield the handheld oximeters from patient contact and contaminants during use and shield patients from contaminants on the handheld oximeters. Because a handheld oximeter is located in a sheath and cannot contaminate patient tissue, the handheld oximeter can be reused.

In an implementation, a sheath includes a top and a body where the top opens to provide an opening where a handheld oximeter can be placed into the body of the sheath. The top of the sheath can be closed onto the body and the closure of the top can be verified by circuits in the handheld oximeter. The circuits can monitor the position of a latch that is connected to the top of the sheath and can latch to the sheath or can monitor the position of a latch that is connected to the sheath and can latch to the top. The circuits can determine when the latch is unlatched and the top is open and not sealed closed to the body. And, the circuits can determine when the latch is latched and the top is closed and sealed to the body.

In an implementation, a sheath communicates sheath status information to a handheld oximeter to verify that the sheath is a validated sheath that is permitted to operate in combination with the handheld oximeter. A validated sheath having a known and trusted configuration facilitates the reuse of a handheld oximeter because the oximeter is known to remain free of contaminants during the use of the oximeter. The communication between the sheath and handheld oximeter can be wireless using near-field communication (NFC) devices and NFC communication protocols or other circuit types and other communication protocols.

The sheath can include windows that allow light from a handheld oximeter to pass through the windows during the use of the oximeter. A first window can be proximate to a display of the handheld oximeter so that the display can be viewed by a user during use. A second window can be proximate to a probe face of a handheld oximeter so that the oximeter can emit light into tissue and collect the light after reflection from the tissue so that oximetry measurements can be made for the tissue. The windows are sealed to the sheath and keep the handheld oximeter from becoming contaminated during use.

The handheld oximeters implementations are entirely self-contained, without any need to connect, via wires or wirelessly, to a separate system unit for making oximetry measurements. The sources and detectors of the oximetry device are arranged in an arrangement having various source-detector pair distances that allow for robust calibration, self-correction, and oximetry measurements (such as spatially-resolved spectroscopy) in a compact probe. Other source-detector arrangements are also possible.

In an implementation, the handheld oximeter is a tissue oximeter that can measure oxygen saturation without requiring a pulse or heartbeat. A tissue oximeter of the invention is applicable to many areas of medicine and surgery, including plastic surgery. The tissue oximeter can make oxygen saturation measurements of tissue where there is no pulse; such tissue, for example, may have been separated or partially separated from the body (e.g., a flap) and will be transplanted to another place in the body. The tissue oximeter can also make oxygen saturation measurements of tissue where there is a weak pulse, such as where perfusion is relatively low.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
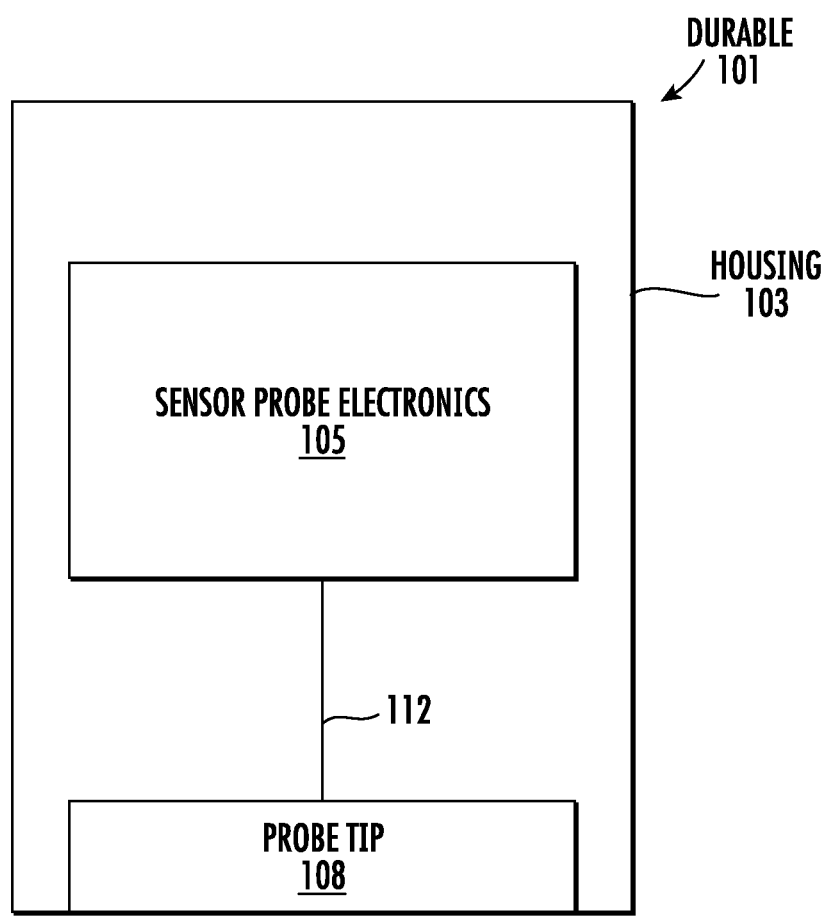
FIG. 1 shows a block diagram of a system unit for measuring various oximetry parameters of patient tissue.

Spectroscopy has been used for noninvasive measurements of various physiological properties in animal and human subjects. Visible (e.g., red light, green light, or both) and near-infrared spectroscopy is often utilized because physiological tissues have relatively low scattering in these spectral ranges. Human tissues, for example, include numerous light-absorbing chromophores, such as oxygenated hemoglobin, deoxygenated hemoglobin, melanin, water, lipid, and cytochrome. The hemoglobins are the dominant chromophores in tissue for much of the visible and near-infrared spectral range and via light absorption, contribute to the color of human tissues. In the visible and near-infrared range, oxygenated and deoxygenated hemoglobins have significantly different absorption features. Accordingly, visible and near-infrared spectroscopy has been applied to exploit these different absorption features for measuring oxygen levels in physiological media, such as tissue hemoglobin oxygen saturation (sometimes referred to as oxygen saturation) and total hemoglobin concentrations.

Various techniques have been developed for visible and near-infrared spectroscopy, such as time-resolved spectroscopy (TRS), frequency-domain techniques such as phase modulation spectroscopy (PMS), and continuous wave spectroscopy (CWS). In a homogeneous and semi-infinite model of physiological media, both TRS and PMS have been used to obtain the absorption coefficients and the reduced scattering coefficients of the physiological medium by use of the photon diffusion approximation, Monte Carlo models, or other techniques. From the absorption coefficients at multiple wavelengths, concentrations of oxygenated and deoxygenated hemoglobins can be determined and from these concentrations, the tissue oxygen saturation can be calculated.

Spatially-resolved spectroscopy (SRS) is one type of visible and near-infrared spectroscopy that allows tissue absorption to be determined independently from tissue scattering, thereby allowing absolute measurements of chromophore concentrations, such as oxygenated and deoxygenated hemoglobins. More specifically, an SRS instrument may emit light into tissue through a light source and collect the diffusely reflected light at two or more detectors positioned at different distances from the light source.

Alternatively, an SRS instrument may emit light from two or more light sources positioned at different distances from one or more detectors. Scattering of light back to the detectors is caused by relative changes of the index of refraction of the tissue and includes Mie scattering from larger structures such as mitochondria (the majority of tissue scattering is a result of mitochondria) and Rayleigh scattering from smaller structures such as intracellular vesicles. Absorption of light is caused by interaction with the tissue's chromophores.

From the reflectance (i.e., the recovered light intensity), which is recovered as a function of distance (e.g., multiple discrete distances of light detectors) from the light source, an SRS instrument can quantify the absorption coefficient and the scattering coefficient of the tissue at a single wavelength.

Multiple wavelengths of light can then be used with SRS to determine oxygenated and deoxygenated hemoglobin concentrations, and therefore, oxygen saturation within the volume of the tissue probed. Further, the wavelengths of the light source or light sources and the relative positions of the light source(s) with respect to a single detector or multiple ones of the detectors, allow tissue oximetry measurements to be made for a predetermined tissue depth. In an embodiment, one or more of the light sources and one or more of the detector source may emit and detect light so that oximetry measurements may be made for one or more predetermined tissue depths.

One field in which visible and near-infrared spectroscopy, such as SRS, is useful is in tissue flap surgery in which a tissue flap is moved from one location on a patient to another location for reconstructive surgery. Visible and near-infrared spectroscopy techniques can be used to measure oxygen saturation in a tissue flap so that the viability of the tissue flap can be determined in surgery and after surgery. Intraoperative tissue flap oximetry probes that employ visible and near-infrared SRS should be able to quickly deliver accurate oxygen saturation measurements under a variety of non-ideal conditions.

Oximetry probes adapted for SRS and other spectroscopies can come into contact with tissue, other surfaces, fluids (both liquid and gas), or other elements that can contaminate the probes. An oximetry probe that contacts tissue, for example, can be contaminated by the tissue, bacteria on the tissue, viruses on the tissue, tissue fluid, debris on the tissue, the environment near the tissue, any one of these substances, other substances, or any combination of these substances. A sheath can shield an oximetry probe from contaminants, but the efficacy of a sheath can be compromised in a number of ways. The ways in which a sheath can be compromised, allowing an oximetry probe to be contaminated, can be known and unknown. For example, a sheath housing an oximetry device may open and allow contaminants to contact the oximetry probe. The sheath opening may be relatively small and not detectable by visual inspection and the small opening may allow contaminants to enter the sheath and contact the oximetry probe. The efficacy of a sheath can be compromised if the sheath has been previously used and the previous use is unknown. The efficacy of a sheath can also be compromised if the sheath is provided from an unknown source and the sterility or sanitation of the sheath is unknown. Either inside or outside surfaces of the sheath, or both, can be contaminated if the sheath is provided by an unknown source. If the previous use of a sheath is unknown and the sheath is reused, contaminants on the sheath from an initial use can be spread during subsequent use of the sheath. Sheaths and the oximetry probes in the sheath may be contaminated in a variety of other ways. Reuse of an oximetry probe after contamination may be precluded or may increase the cost of reuse due to the cost of sanitizing or sterilizing the oximetry probe. Oximetry probes and sheaths of the present invention are directed toward improved sanitation, sterilization, or both.

FIG. 1 shows a system unit 101 for measuring various parameters of tissue in a patient. System unit 101 is sometimes referred to as a durable system unit because the unit is reusable, such as when the unit is used in combination with a protective sheath. The parameters of the tissue measured by the system unit may include an oxygen saturation level (relative oxygen saturation, absolute oxygen saturation, or both), a total hemoglobin concentration, an oxygenated hemoglobin concentration, an deoxygenated hemoglobin concentration, blood flow, pulse rate, a signal level of light reflected from the tissue, melanin concentration of tissue, homogeneity of a tissue quality, other tissue parameters, or any combination of the parameters. The system unit includes housing 103, sensor probe electronics 105, and a probe tip 108, which is connected to the sensor probe electronics via a wired connection 112. Connection 112 may be an electrical connection, an optical connection, or another wired connection including any number of wires (e.g., one, two, three, four, five, six, or more wires or optical fibers), or any combination of these or other types of connections. In other implementations, connection 112 may be a wireless connection, such as via a radio frequency (RF) or infrared (IR) connection.

Typically, the system unit is used by placing the probe tip in contact to tissue (e.g., skin) or close proximity to tissue (e.g., an internal organ that is located inside of a body) at a site where tissue parameter measurements are desired. The system unit causes an input signal to be emitted by the probe tip into the tissue (e.g., human tissue). There may be multiple input signals, and these signals may have varying or different wavelengths of electromagnetic radiation. The intensity of the emitted wavelengths of radiation may be time modulated by a digital-to-analog converter that is coupled between the processor and the LEDs. The intensity of the radiation may be sinusoidally modulated, square wave modulated, or modulated by another function. The processor may transmit a digital sinusoidal signal to the digital-to-analog converter, which converts the signal into an analog signal that is transmitted to the LEDs. Sinusoidal light that is emitted and detected can be correlated so that the detected light can be discriminated from background light that generally has a constant intensity relative to the modulated light. The input signal is transmitted into the tissue and reflected from the tissue, absorbed by the tissue, or transmitted through the tissue.

Then, after transmission through the tissue or reflection from the tissue, the signal is received at the probe tip. This received signal is received and analyzed by the sensor probe electronics. Based on the received signal, the sensor probe electronics determine various parameters of the tissue, such as an oxygen saturation level, a total hemoglobin concentration, an oxygenated hemoglobin concentration, an deoxygenated hemoglobin concentration, a blood flow, a pulse, a signal level of light reflected from the tissue, melanin concentration of tissue, other tissue parameters, or homogeneity of any one or more of these parameters. One or any combination of these parameters can be displayed on a display screen of the system unit.

In an implementation, the system unit is a tissue oximeter, which can measure oxygen saturation and hemoglobin concentration, without requiring a pulse or heartbeat. A tissue oximeter of the invention is applicable to many areas of medicine, surgery (including plastic surgery and spinal surgery), post-surgery, athlete monitoring, and other uses. The tissue oximeter can make oxygen saturation and hemoglobin concentration measurements of tissue where there is no pulse, such as tissue that has been separated from the body (e.g., a tissue flap) and will be transplanted to another place in the body.

Aspects of the invention are also applicable to a pulse oximeter. In contrast to a tissue oximeter, a pulse oximeter requires a pulse in order to function. A pulse oximeter typically measures the absorbance of light due to the pulsing arterial blood.

There are various implementations of systems and techniques for measuring oxygen saturation, such as discussed in U.S. Pat. Nos. 6,516,209, 6,587,703, 6,597,931, 6,735,458, 6,801,648, and 7,247,142. There are various implementations of systems and techniques for measuring oxygen saturation, such as discussed in U.S. patent applications 62/959,764, 62/959,778, 62/959,787, 62/959,795, and 62/959,808, filed Jan. 10, 2020; Ser. No. 17/146,182, 17/146,186, 17/146,190, 17/146,194, 17/146,197, and 17/146,201, filed Jan. 11, 2021; and Ser. No. 29/720,112, 29/720,115, 29/720,120, and 29/720,122, filed Jan. 9, 2020. These patent applications are incorporated by reference along with all other references cited in these applications.

Figure 2:
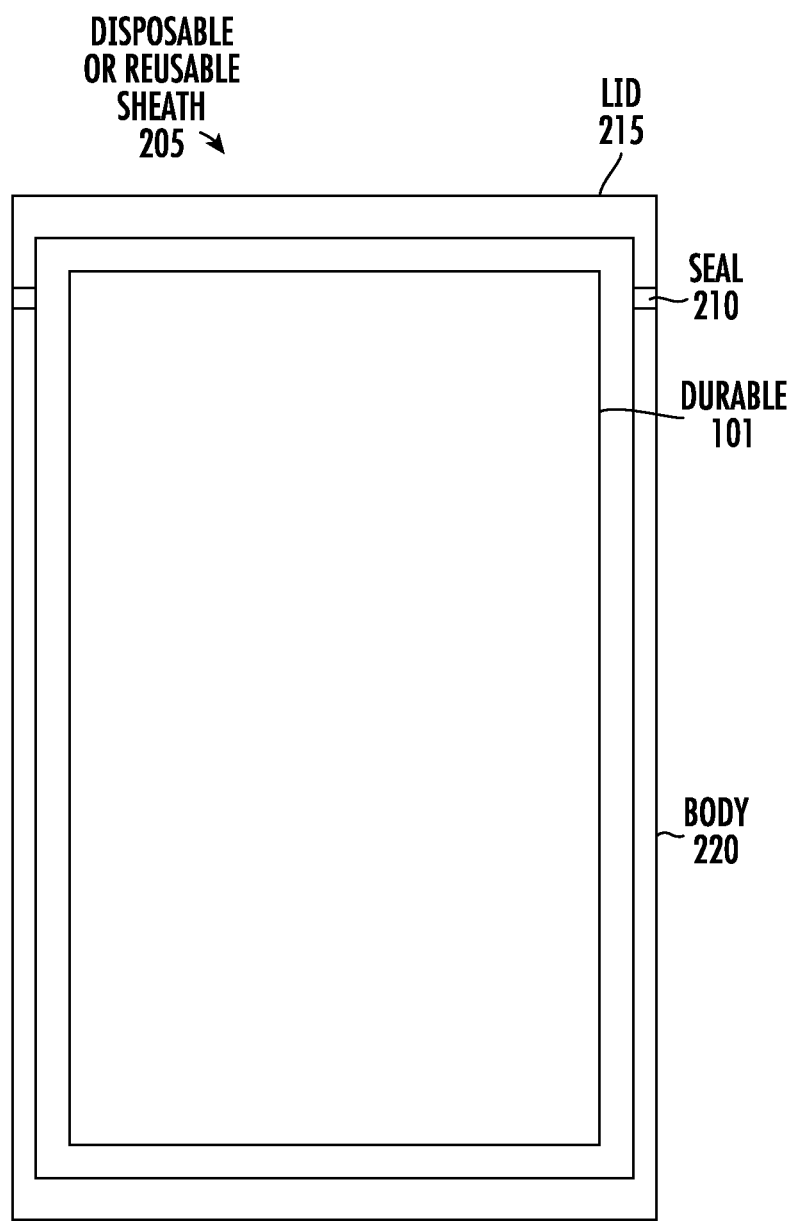
FIG. 2 shows a block diagram of the system unit housed in a sheath.

FIG. 2 shows system unit 101 housed in a sheath 205. The sheath includes a lid 215 and a body 220, which may be sealed to the lid via a seal 210. The lid may be separable from the body or may be connected to the body, such as via a hinge. The hinge may allow the lid to rotate to seal the lid to the body. The sheath may be a disposable sheath or a sheath that is reusable. For example, the system unit and sheath may travel with a patient from surgery (e.g., use) to post-surgery (e.g., reuse) for tissue monitoring.

With the lid opened, the system unit may be inserted into the sheath, and thereafter the lid may be sealed to the body to house and seal the system unit in the sheath. The system unit may then be used to make tissue parameter measurements in the sealed environment provided by the sheath. The sheath can protect a patient from contacting contaminants on the system unit, and the sheath can protect the system unit from contacting elements that the sheath contacts, such as tissue, tissue fluid, biological agents (e.g., bacteria, viruses, prions, and pyrogens), pyrogens, debris, and other contaminants. When the lid is open and the seal is broken, the system unit may be removed from the sheath. Because the system unit is sealed into the sheath by the body, lid, and seal, the system unit can remain relatively clean, sanitized, or sterile for reuse. The sheath can also protect the tissue of a patient from contacting elements that are on a system unit that is inside the sheath. For example, the sheath can prevent patient tissue from contacting bacteria, viruses, prions, pyrogens, other contaminants, or any one of these contaminants that might be on the system unit.

The sheath can also protect the tissue of a patient from contacting elements that are on a system unit that is inside the sheath. The sheath can prevent patient tissue from contacting bacteria, viruses, prions, pyrogens, other contaminants, or any one of these contaminants that might be on the system unit from passing through the sheath seal and contacting patient tissue.

Figure 3:
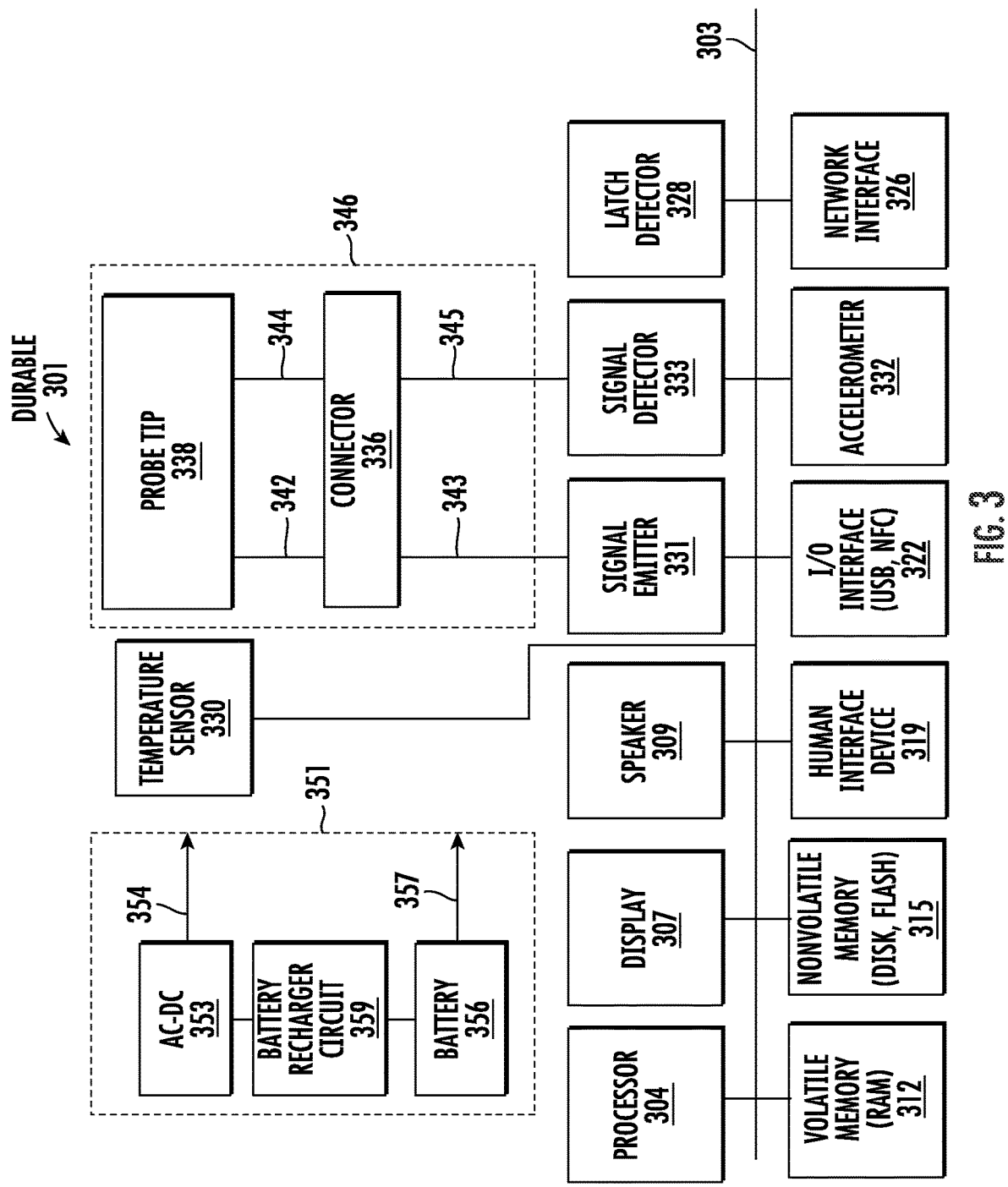
FIG. 3 shows a block diagram of the system unit, in an implementation.

FIG. 3 shows a block diagram of system unit 301, in an implementation. The system unit includes a processor 304, display 307, speaker 309, signal emitter 331, signal detector 333, volatile memory 312, nonvolatile memory 315, human interface device (HID) 319, input-output (I/O) interface 322, network interface 326, latch detector 328, temperature sensor 330, and accelerometer 332. These components are housed within housing 103. Different implementations of the system may include any number of the components described, in any combination or configuration, and may also include other components not shown.

The components are linked together via a bus 303, which represents the system bus architecture of the system unit. Although FIG. 3 shows one bus that connects to each component of the system unit, bus 303 is illustrative of any interconnection scheme that links the components of the system unit. For example, one or more bus subsystems can interconnect one or more of the components of the system unit. Additionally, the bus subsystem may interconnect components through one or more ports, such as an audio port (e.g., a 2.5-millimeter or 3.5-millimeter audio jack port), a universal serial bus (USB) port, or other port. Components of the system unit may also be connected to the processor via direct connections, such as direct connections through a printed circuit board (PCB).

In an implementation, system unit 301 includes a sensor probe 346. The sensor probe includes a probe tip 338 and a connector 336. The probe tip is connected to the connector via a first communication link 342 and a second communication link 344. First communication link 342 may include an electrical wire, a set of electrical wires (e.g., a ribbon cable), a waveguide (e.g., a fiber optic cable), a set of waveguides (e.g., a set of fiber optic cables), a wireless communication link, or any combination of these types of links. The second communication link may include an electrical wire, a set of electrical wires (e.g., a ribbon cable), a waveguide (e.g., a fiber optic cable), a set of waveguides (e.g., a set of fiber optic cables), a wireless communication link, or any combination of these types of links. The electrical wire or sets of electrical wires of the first communication link, the second communication link, or both can include one or more electrical traces on a printed circuit board.

The connector connects (e.g., removably connects) the probe tip, the wires, waveguides, or any combination of these elements to the signal emitter and signal detector of the system unit. For example, a communication link 343 may connect the signal emitter to the connector and a communication link 345 may connect the signal detector to the connector. Each of the communication links 343 and 345 may include an electrical wire, a set of electrical wires (e.g., a ribbon cable) one waveguide, a set of waveguides, a wireless communication link, or any combination of these links. Each communication link can also include one or more electrical traces on a printed circuit board. For example, the connector may include one or more connectors that are mounted on a PCB. Communication links 342, 344, or either one of these links may be ribbon cables that connect to the probe tip and connect to connectors mounted on a PCB. In this implementation, communication links 343 and 345 can be electrical traces on the PCB that link to the single emitter, signal detector, or both. In this implementation, the signal emitters and signal detectors may be electrical emitters and detectors that control light emitters, light detectors, or both in the probe tip.

In an implementation, where the probe tip is separable from the system unit 301, connector 336 may have a locking feature, such as an insert connector that may twist or screw to lock. If so, the connector is more securely held to the system unit and it will need to be unlocked before it can be removed. This will help prevent the accidental removal of the probe tip from the system unit.

The connector may also have a first keying feature, so that the connector can only be inserted into a connector receptacle of the system unit in one or more specific orientations. This will ensure that proper connections are made.

The connector may also have a second keying feature that provides an indication to the system unit of a type of probe (e.g., a probe from many different types of probes) that is attached. The system unit may be adapted to make measurements for a number of different types of probes. When a probe is inserted in the system unit, the system uses the second keying feature to determine the type of probe that is connected to the system unit. Then the system unit can perform the appropriate functions, use the appropriate algorithms, or otherwise make adjustments in its operation for the specific probe type.

In an implementation, the connector and system unit are communicatively coupled (e.g., wired or wirelessly) to transmit and receive information regarding the type of probe being attached to the system unit. The connector and system unit may be electrically coupled by electrical connectors or by radio frequency circuits. For example, the connector and system unit may each include a near field communication device that transmits and receives information for the type of probe being attached to the system unit. Then the system unit can perform the appropriate functions, use the appropriate algorithms, or otherwise make adjustments in its operation for the specific probe type.

In an implementation, signal emitter 331 includes one or more light sources that emit light at one or more specific wavelengths. In a specific implementation, the light sources emit five or more wavelengths of light (e.g., 730 nanometers, 760 nanometers, 810 nanometers, 845 nanometers, and 895 nanometers). Other wavelengths of light are emitted by the light sources, including shorter and longer wavelengths of light in other implementations. The signal emitter may include one or more laser diodes or one or more light emitting diodes (LEDs). In an implementation, a light source is a multispectral light source and a detector is a spectrometer detector.

In an implementation, signal emitter 331 includes one or more light sources that emit light at one or more specific wavelengths. In a specific implementation, the light sources emit five or more wavelengths of light (e.g., 730 nanometers, 760 nanometers, 810 nanometers, 845 nanometers, and 895 nanometers). Other wavelengths of light are emitted by the light sources, including shorter and longer wavelengths of light in other implementations. The signal emitter may include one or more laser diodes or one or more light emitting diodes (LEDs).

In an implementation, signal emitter 331 is an emitter that emits electrical signals to one or more light sources, which may emit light based on the received electrical signals. In some implementations, the signal emitter includes one or more light sources and electrical signal emitters that are connected to the light sources.

In an implementation, signal detector 333 includes one or more photodetectors capable of detecting the light at the wavelengths produced and emitted by the signal emitter. In another implementation, the signal detector 333 is an electrical signal detector that detects electrical signals generated by one or more photodetectors. In another implementation, the signal detector includes one or more photodetectors and one or more electrical detectors that are connected to the photodetectors.

In an implementation, HID 319 is a device that is adapted to allow a user to input commands into the system unit. The HID may include one or more buttons, one or more slider devices, one or more accelerometers, a computer mouse, a keyboard, a touch interface device (e.g., a touch interface of display 307), a voice interface device, or another HID.

In an implementation where the HID is an accelerometer and the system unit is a handheld unit, the accelerometer may detect movements (e.g., gestures) of the system unit where the system unit may be moved by a user. Movements may include a left movement, right movement, forward movement, back movement, up movement, down movement, one or more rotational movements (e.g., about one or more axes of rotation, such as the x-axis, y-axis, z-axis, or another axis), any combinations of these movements, or other movements.

Information for the various movements detected by the accelerometer may be transmitted to the processor to control one or more systems of the system unit. For example, an upward movement (e.g., a lifting movement) may be transmitted to the processor for powering on the system unit. Alternatively, if the system unit is set down and left unmoved for a predetermined period of time, then the processor may interpret the lack of movement detected by the accelerometer as a standby mode signal and may place the system unit in a standby power mode (a lower power mode than a normal operation mode where oximetry measurements can be made by the system unit), or a power-down signal and may power down the system unit.

When the system unit is powered on, information for a left movement or a right movement detected by the accelerometer and transmitted to the processor may be used by the processor to control the system unit. For example, a left or right movement of the system unit may be used by the processor to change menu items displayed on the display. For example, the processor may use the information for a left movement to scroll menu items on the display to the left (e.g., scroll a first menu item left and off of the display to display a second menu item on the display). The processor may use the information for a right movement of the system unit to scroll menu items to the right (e.g., scroll a first menu item right and off of the display, and display a second menu item on the display).

The HID and processor may be adapted to detect and use various movements to activate a menu item that is displayed on the display. For example, information for an upward movement or a downward movement may be detected and used to activate a menu item that is displayed on the display. For example, if a user is prepared to take an oximeter measurement and a menu option is displayed for taking an oximeter measurement, a quick downward movement of the system unit may start a measurement when the probe tip is placed in contact with tissue The HID may include one or more accelerometers to detect motion in various directions (e.g., linear, rotational, or both). The accelerometers can include one or more capacitive micro-electro-mechanical system (MEMS) devices, one or more piezoresistive devices, one or more piezoelectric devices, or any combination of these devices.

In an embodiment, accelerometer 332 is adapted to detect relatively high G-force accelerations associated with a shock that the system unit experiences. The shock may be from bumping the system into something, dropping the system unit (e.g., dropping the system unit on a table or the floor), or other shock events. In an implementation, if the accelerometer indicates to the processor that a shock event has occurred, the processor can take a number of actions. For example, the processor can shut down the system unit. The processor can display one or more messages on the display. The messages may indicate that the system unit should be recalibrated. The message may indicate that contact between the system unit and the sheath should be checked. The accelerometer may include one or more capacitive micro-electro-mechanical system (MEMS) devices, one or more piezoresistive devices, one or more piezoelectric devices, or any combination of these devices.

In an implementation, the latch detector 328 is adapted to detect whether a latch of the sheath is latched or unlatched. If the latch is latched (e.g., latched and detected as being latched), then the system unit is housed and enclosed in the sheath. In this configuration, with the system unit housed and enclosed in the sheath, the system unit may not be contaminated by material contacting the outside surface of the sheath. If the latch is unlatched and the system unit is in the sheath, then the system unit might be contaminated with material contacting the outside surface of the sheath. That is, the seal that seals the lid of the sheath to the body of the sheath may be unsealed (i.e., opened) and contaminates may pass from outside of the sheath to the inside of the sheath where the system unit is located.

In an implementation, at least a first portion of the latch is metal. Other portions of the latch may be metal or other material, such as a plastic material. The first portion of the latch is a first distance from the latch detector when the latch is latched and is a second distance from the latch detector when the latch is unlatched. The first distance is less than the second distance.

In an implementation, the latch detector includes an inductor that can inductively couple to the first portion of the latch. The inductor can be driven with a direct current or an alternating current and thus detect when the first portion of the latch moves toward the latch detector or away from the latch detector. The latch detector can be calibrated so that the latch detector can detect when the latch moves to the first distance away from the latch detector or farther than the first distance away from the latch detector. The latch detector can include an analog-to-digital converter, a digital signal processor (DSP), or both that digitize and analyze the current flowing through the inductor. One or both of these circuits can communicate the digitalized information to the processor that can determine whether the latch is open or closed. The processor can display a message on the display to indicate whether the latch is open or closed, whether the seal for the sheath is sealed or unsealed, warn of potential contamination, or other messages associated with the latch being opened or closed.

In an embodiment, the latch detector is a capacitive detector that can capacitively couple to the latch. The capacitive detector can detect the latch in the latched position at a first distance from the capacitive detector and moving away from the latched position and the first distance. In an embodiment, the latch detector is a magnetic detector that can magnetically detect that the latch is latched. That is, the magnetic detector can detect the latch in the latched position at a first distance from the magnetic detector and moving away from the latched position and the first distance. In an embodiment, the latch detector is a mechanical detector, such as a mechanical interlock.

The nonvolatile memory 315 may include a FLASH memory, other nonvolatile solid-state storage (e.g., USB flash drive), battery-backed-up volatile memory, tape storage, reader, and other similar media, and combinations of these. In some implementations, the nonvolatile memory includes a mass disk drive, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc). The volatile memory may include a random access memory (RAM).

The processor may include a microcontroller, a microprocessor, an application specific integrated circuit (ASIC), programmable logic (e.g., field programmable gate array), or any combination of these circuits. The processor may include multiple processors or a multicore processor, which may permit parallel processing of information.

In an implementation, the system unit is part of a distributed system. In a distributed system, individual systems are connected to a network and are available to lend resources to another system in the network as needed. For example, a single system unit may be used to collect results from numerous sensor probes at different locations.

Aspects of the invention may include software executable code, firmware (e.g., code stored in a read only memory (ROM) chip), or both. The software executable code or firmware may embody algorithms used in making oxygen saturation measurements of the tissue. The software executable code or firmware may include code to implement a user interface by which a user uses the system, displays results on the display, selects or specifies parameters that affect the operation of the system, or execute algorithms and calculations to generate a result.

Further, a computer-implemented or computer-executable version of the invention may be embodied using, stored on, or associated with a computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on a mass storage device. Source code of the software of the present invention may also be stored or reside on a mass storage device (e.g., hard disk, magnetic disk, tape, or CD-ROM). As a further example, code of the invention may be transmitted via wires, radio waves, or through a network such as the Internet. Firmware may be stored in a ROM of the system.

Computer software products may be written in any of various suitable programming languages, such as C, C++, C#, Pascal, Fortran, Perl, MATLAB (from MathWorks, www-.mathworks.com), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows XP, Windows XP x64 Edition, Windows Vista, Windows CE, Windows 7, Windows 8, Windows 10, Windows Mobile), Linux, HP-UX, UNIX, Solaris, Mac OS X, Alpha OS, AIX, IRIX32, or IRIX64. Microsoft Windows is a trademark of Microsoft Corporation. Other operating systems may be used, including custom and proprietary operating systems.

Furthermore, the system may be connected to a network and may communicate with other systems using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, and 802.11n, just to name a few examples). For example, signals from a system may be transferred, at least in part, wirelessly to components or other systems or computers.

In an embodiment, through a Web browser or other interface executing on a computer workstation system or another device (e.g., a laptop computer, smartphone, or personal digital assistant), a user accesses the system unit of the invention through a network such as the Internet. The user will be able to see the data being gathered by the system unit. Access may be through the World Wide Web (WWW). The Web browser is used to download Web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 4:
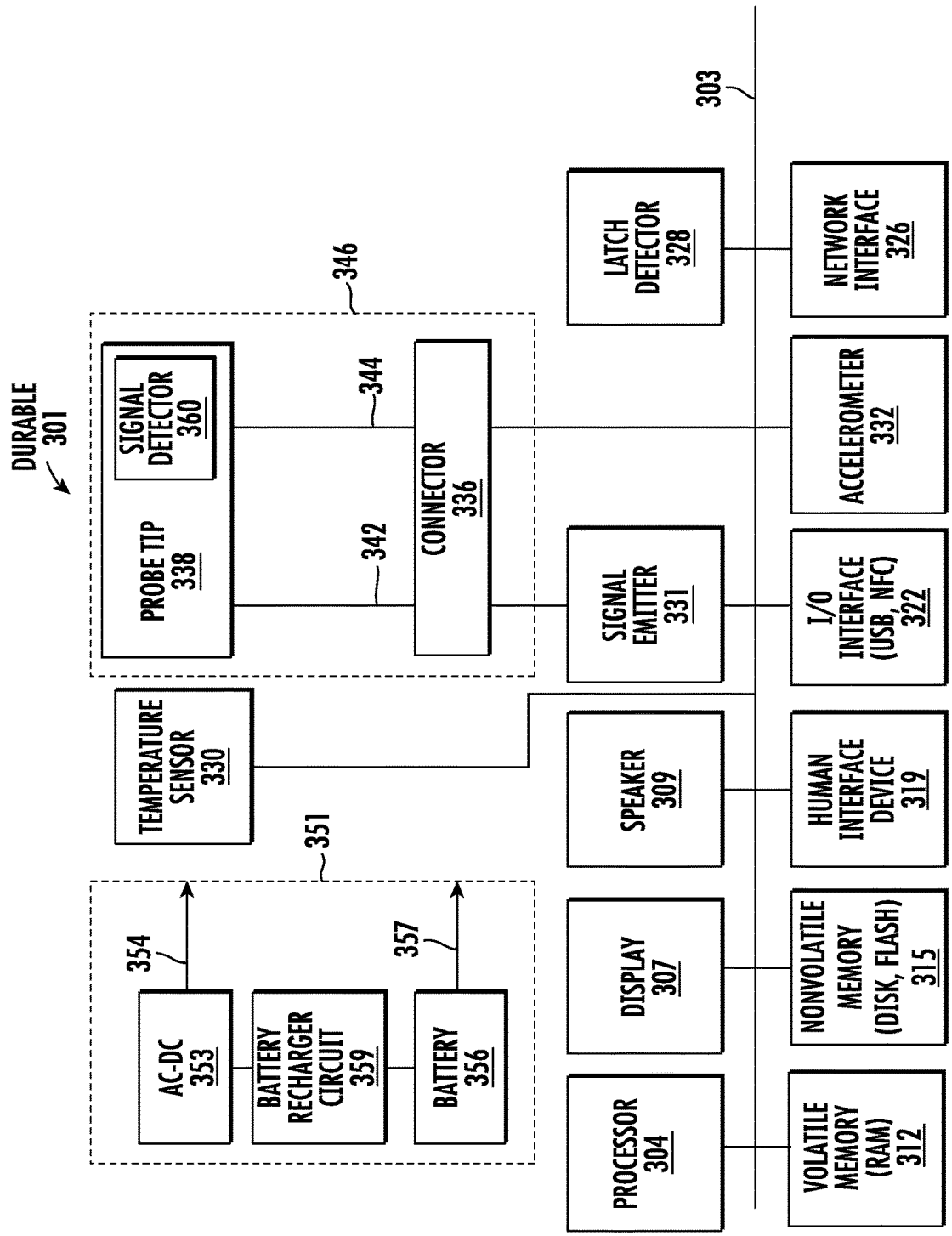
FIG. 4 shows a block diagram of the system unit, in an implementation.

FIG. 4 shows a block diagram of system unit 401, in an implementation. System unit 401 is similar to system unit 301 but differs in that the signal detector 344 is located in probe tip 346. A wire or set of wires (e.g., a ribbon cable) may connect the signal detector to the bus and processor. For example, a ribbon cable that is connected to the signal detector may also be connected to a connector or socket mounted on a PCB that the processor and other circuits are mounted on. The signal detector may be located at a probe face of the probe tip. The signal emitter may be optically located behind the probe face of the probe tip.

Figure 5:
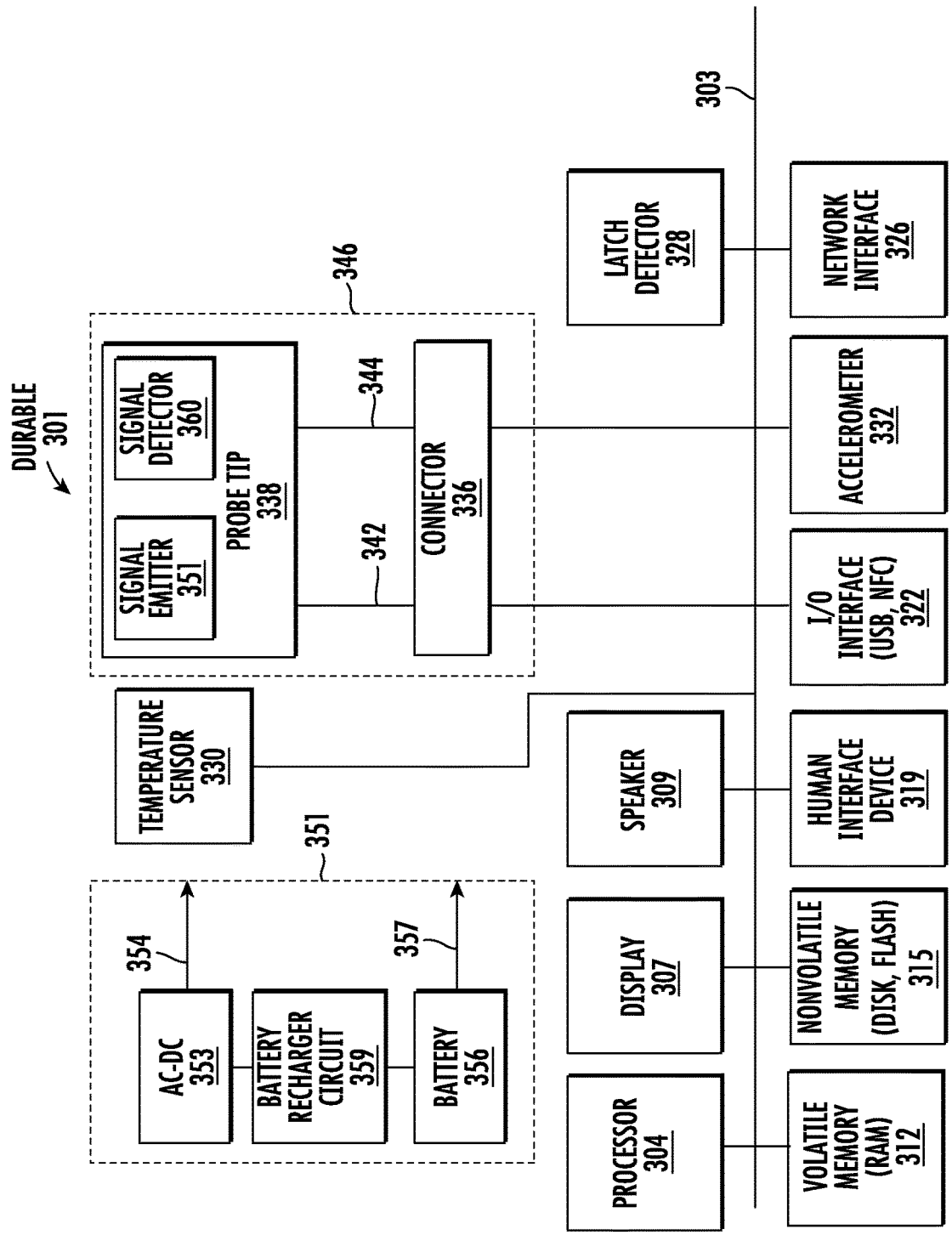
FIG. 5 shows a block diagram of the system unit, in an implementation.

FIG. 5 shows a block diagram of system unit 501, in an implementation. System unit 501 is similar to system units 301 and 401 but differs in that the signal emitter 331 and the signal detector 344 are located in probe tip 346. A wire or wires (e.g., one or more ribbon cables) may connect the signal emitter, the signal detector, or both to the bus and processor. A first ribbon cable may connect the signal emitter to the bus and processor and a second ribbon cable may connect the signal detector to the bus and processor. For example, the first ribbon cable that is connected to the signal emitter may also be connected to a connector or socket mounted on a PCB that the processor and other circuits are mounted on, and the second ribbon cable that is connected to the signal detector may also be connected to a connector or socket mounted on the PCB. The signal detector may be located at a probe face of the probe tip. The signal emitter may be optically located behind the probe face of the probe tip.

In an implementation, connector 336 includes a locking feature, such as an insert connector that inserts into a connecting port and then twists or screws to lock. If so, the connector is more securely held to the system unit and it will need to be unlocked before it can be removed. This will help prevent accidental removal of the probe.

In an implementation, connector 336 includes one or more PCBs that are connected to one or more wires (e.g., ribbon cables) that connect to the signal emitter, the signal detector, or both. For example, a first ribbon cable may connect to a first PCB that connects to the signal emitter. A second ribbon cable may connect to a second PCB that connects to the signal detector. connect a firs Block 351 shows a power block of the system unit having both AC and battery power options. In an implementation, the system includes an AC-to-DC converter 353, such as a full-wave rectifier. The converter takes AC power from a wall socket, converts AC power to DC power, and the DC output is connected (indicated by an arrow 354) to the components of the system unit needing power.

In an implementation, the system is battery operated. The DC output of a battery 356 is connected (indicated by an arrow 357) to the components of the system unit needing power. The battery may be recharged via a recharger circuit 359, which received DC power from the AC-to-DC converter. The AC-to-DC converter and recharger circuit may be combined into a single circuit. In an implementation, the battery is rechargeable via magnetic charging or induction charging.

In an implementation, block 351 is a battery module that includes one or more batteries that power the components of the system unit. The batteries may be rechargeable or disposable batteries. The block may not include the AC-to-DC converter. Block 351 may be a block that is integrated with the system unit or is separable from the system unit.

Figure 6:
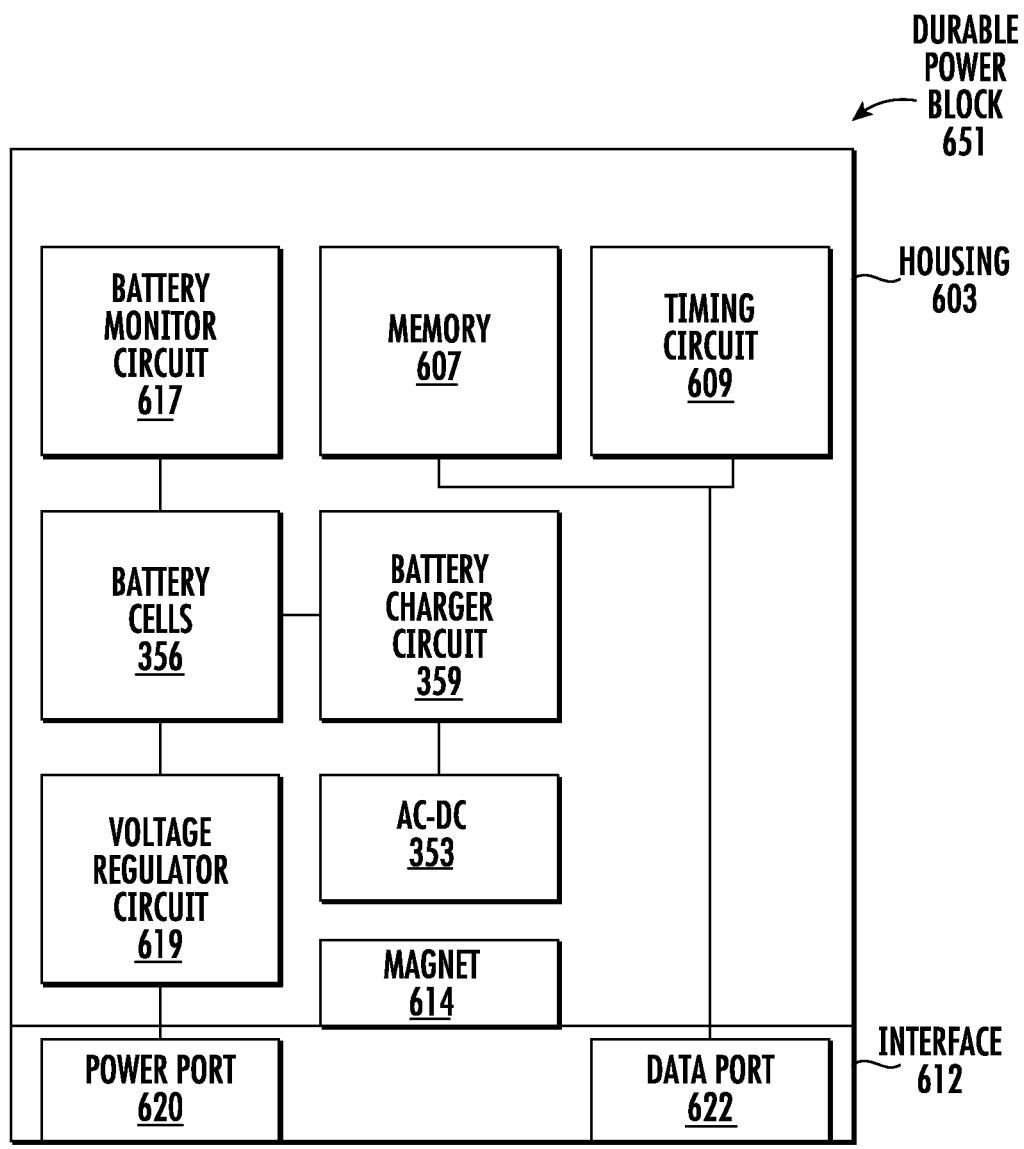
FIG. 6 shows a diagram of the power block of the system unit, in an implementation.

FIG. 6 shows block 651 that is a power block, in an implementation. Block 651 is similar to block 351 but may include a battery monitor 617, a voltage regulator circuit 619, a memory 607, a timing circuit 609, an interface 612, which includes a power port 620 and a data port 622, a magnet 614, other circuits, or any combination of these circuits.

Battery monitor 617 may be connected to the battery cells 356 and may monitor the capability of the battery cells. For example, the battery monitor may determine a current charge state, such as a percentage of the total possible charge. The battery monitor may determine the charge capacity of the battery cells. The charge capacity may be a percentage of the charge capacity compared to the charge capacity of the battery cells when new. The battery monitor may determine the maximum power delivery capability of the battery.

The battery cells may be disposable battery cells, such as alkaline battery cells, or rechargeable battery cells, such as nickel metal hydride, lithium battery cells (e.g., Li/FeS2 size AA, AAA, N, CR123, 18650, or others), lithium polymer, or other types of cells. The power back may include four battery cells that are AA size cells that output 1.5 volts. The four batteries may be in series to output 6 volts, or may be in series and parallel to output 3 volts.

Voltage regulator circuit 619 may be connected between the battery cells and the power port of the battery interface 612. The voltage regulator circuit conditions the voltage output from the battery to output an approximately constant voltage. The voltage regular circuit may also include a DC-to-DC converter that converts a first voltage output from the battery cells to a second voltage that is different from the first voltage.

The timing circuit is a circuit that determines the amount of time length that the battery has been used. Information for the amount of time may be stored in the memory and may be transferred through the data port to the processor when the processor queries the memory for the information.

In an embodiment, the memory may also store an encrypted identifier that identifies the power block. The processor may be adapted to retrieve the encrypted identifier via the power blocks data port. The processor or another decryption circuit of the system unit may decrypt the encrypted identifier and may identify the power block based on the identifier after decryption. The identifier may identify the manufacturer of the power block or may identify other information about the power block, such as the manufacturing date, the battery cell type, battery cell voltage, elapsed usage time, or any combination of these elements. In an implementation, if the identifier is not a known identifier that is known to the system unit, then the processor with not allow the system unit to operate with the power block. That is, the system unit will not operate with a power block manufactured by an unknown manufacturer. Allowing the system unit to operate with known (e.g., authorized) power blocks, the system unit is assured that the power provided by the power block is within the operating specifications of the system unit. Therefore, the circuits, signal emitters, signal detectors, and other elements of the system unit will operate within predetermined parameters and will not operate outside of the predetermined parameters. Also, using a known battery from a known manufacturer provides that the stem unit will operate for a known period of time so that the system unit will not run out of battery power during a medical procedure, such as a surgery. Operating the system unit according to predetermined parameters, facilitates the system unit making accurate and reliable oximetry measurements.

In an implementation, nonvolatile memory 315 stores one or more identifiers for one or more power blocks that may operate with the system unit. The processor may compare the identifier for the power pack that has been decrypted to the one or more identifiers retrieved from the nonvolatile memory to determine whether the power block will be allowed to operate with the system unit. If the power block is not authorized for use with the system unit, the processor may cause a message to be displayed on the display that indicates that the power block is not authorized for use with the system unit. If the power block is authorized to operate with the system unit, then the system unit may operate to make oximetry measurements without displaying information on the display about the authenticity or the inauthenticity of the power block.

In an implementation, the memory of the power block stores an indicator that indicates whether the battery has been previously used. The indicator may be the time information for the amount of time that the power block has operated. In an embodiment, a time stored in memory that is greater than zero is an indicator that the power block has been previously used. In another embodiment, a zero use time stored in the memory is an indicator that the power block has not previously been used. Alternatively, the indicator may be an identifier of a system unit that the power block has been connected to and provided power to. For example, the nonvolatile memory of the system unit may store an identifier of a system unit. The processor of the system unit may transfer the system identifier of the system unit to the power block for storage in the power block's memory.

When the power block is attached to a system unit, the processor of the system unit may query the power block's memory to retrieve any system identifier that may be stored in the power block's memory. In an implementation, if a system identifier retrieved from the power block's memory is different from the system identifier of the system unit that retrieved the system unit from the power block's memory, then the system unit will not operate with the power block. The implementation attempts to ensure that a power block is fully charged and can be used for the duration of a medical procedure (e.g., a surgery) without the power block running out of stored energy. Ensuring that a power block is unused prior to using the power block during a medical procedure provides that the power block will not run out of power during the procedure and minimize risk to a patient. That is, patient risk is lowered if a system unit used during a procedure does not run out of power and can be used for patient monitoring when required.

In an implementation, when the power block is attached to a system unit, the processor of the system unit may query the power block's memory to retrieve the time information for the amount of time that the power block has operated. In an implementation, if the system unit determines that the power block has been previously used based on the time information, then the system unit will not operate with the power block. Similar to the embodiment described immediately above, ensuring that a power block is unused prior to using the power block during a medical procedure provides that the power block will not run out of power during the procedure and minimize risk to a patient.

The power block may include one more magnets 614 that are arranged in an arrangement, such as a square, a rectangular, or another arrangement. A system unit may also have one or more magnets or one or more metal plates (e.g., ferromagnetic plates) that are arranged in an arrangement that is complementary to the arrangement of magnets in the power block. The magnets of the power block may attract the magnets or metal plates of the system unit when the power block is placed in contact with the system unit. The magnetic attraction between the magnets or plates may hold the power block in place when the system unit is being used.

The power block may include one more plates (e.g., ferromagnetic plates) that are arranged in an arrangement, such as square, rectangular, or another arrangement. The system unit may include one or more magnets that are arranged in a complementary arrangement. The magnets of the system unit may magnetically attract the metal plates of the power block when the power block is placed in contact with the system unit. The magnetic attraction between the magnets and plates may hold the power block in place when the system unit is being used.

In an implementation, the power port of the power block includes at least two electrical contacts (e.g., a power contact and a ground contact) and the data port includes at least two electrical contacts (e.g., a data line and a shared ground contact with the power port). The electrical contacts are arranged in an arrangement, such as in a row, in a square, in a rectangle, another arrangement. The system unit includes a power port that includes at least two electrical contacts (e.g., a power contact and a ground contact) and includes a data port that includes at least two electrical contacts (e.g., a data line and a shared ground contact with the power port). The arrangement of the electrical contacts is complementary to the electrical contacts of the power block.

When the power block is placed in contact with the system unit, the magnetic attraction between the magnets or between the magnets and metal plates forces the electrical contacts of the power port in the system unit into contact with the electrical contacts of the power port of the power block. Also, the magnetic attraction forces the electrical contacts of the data port in the system unit into contact with the electrical contacts of the data port of the power block. As such, electrical power can be transferred from the power block to the system unit to power the circuits and other elements of the system unit, and data can be transferred between the power block and the system unit.

Figure 7:
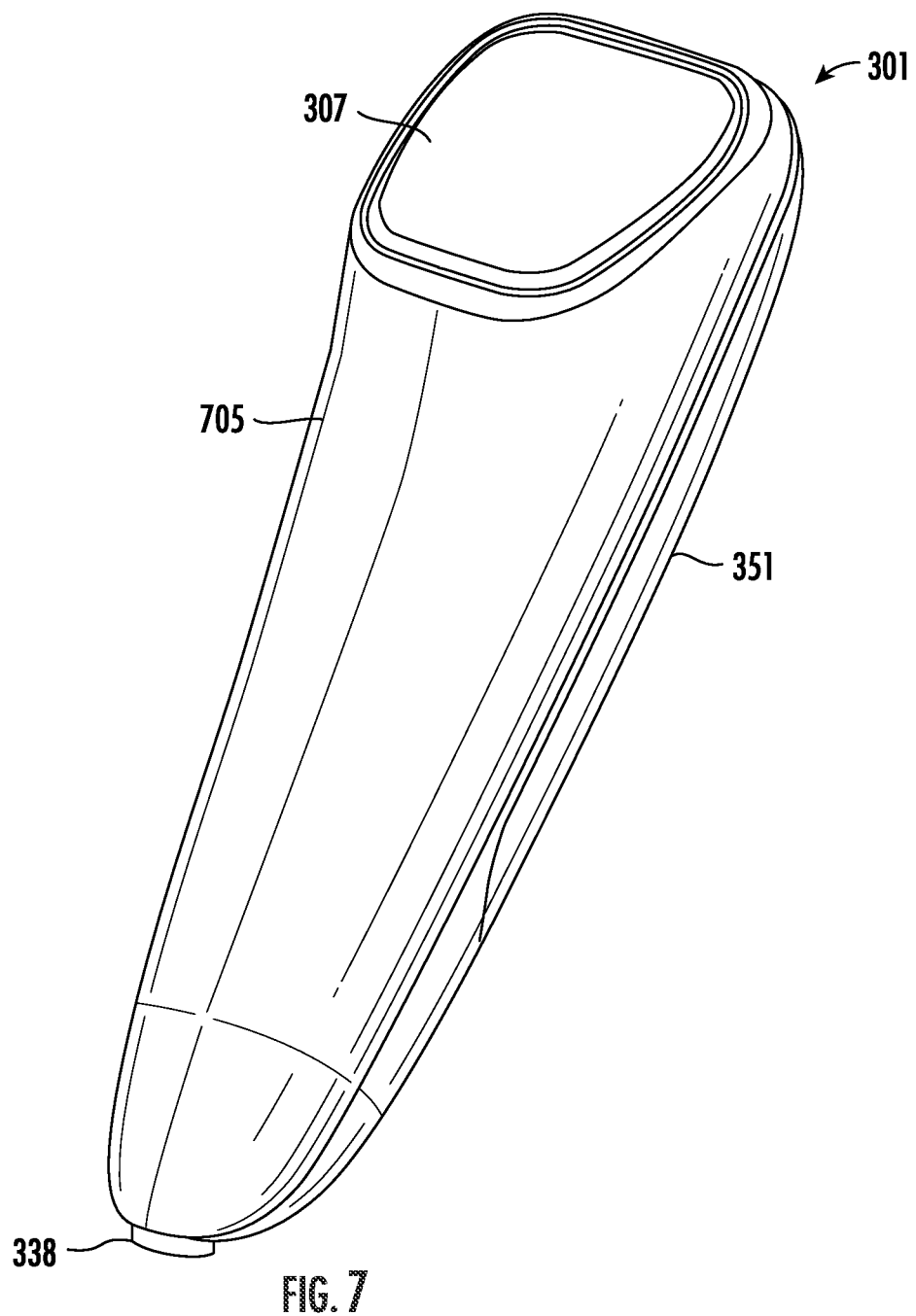
FIG. 7 shows a perspective view of the system unit and power block.

FIG. 7 shows a perspective view of the system unit 301 and power block 351 coupled to the system unit, in an implementation. The display 307 of the system unit is located at a first end of the system unit and the probe tip 338 is located at a second end of the system unit where the first and second ends of proximal and distal ends of the unit. The housing of the system unit tapers from the first end to the second end. The described circuit elements are housed in the housing 705 of the system unit. housing 705 of the system unit. When the second window of the sheath is in contact with tissue, the first window of the sheath and the display of the system unit faces away from the tissue for easy visibility of the display. In an implementation where the system unit is used without a sheath, when the probe face of the system unit is in contact with tissue, the display faces away from the tissue for easy visibility of the display.

Figure 8:
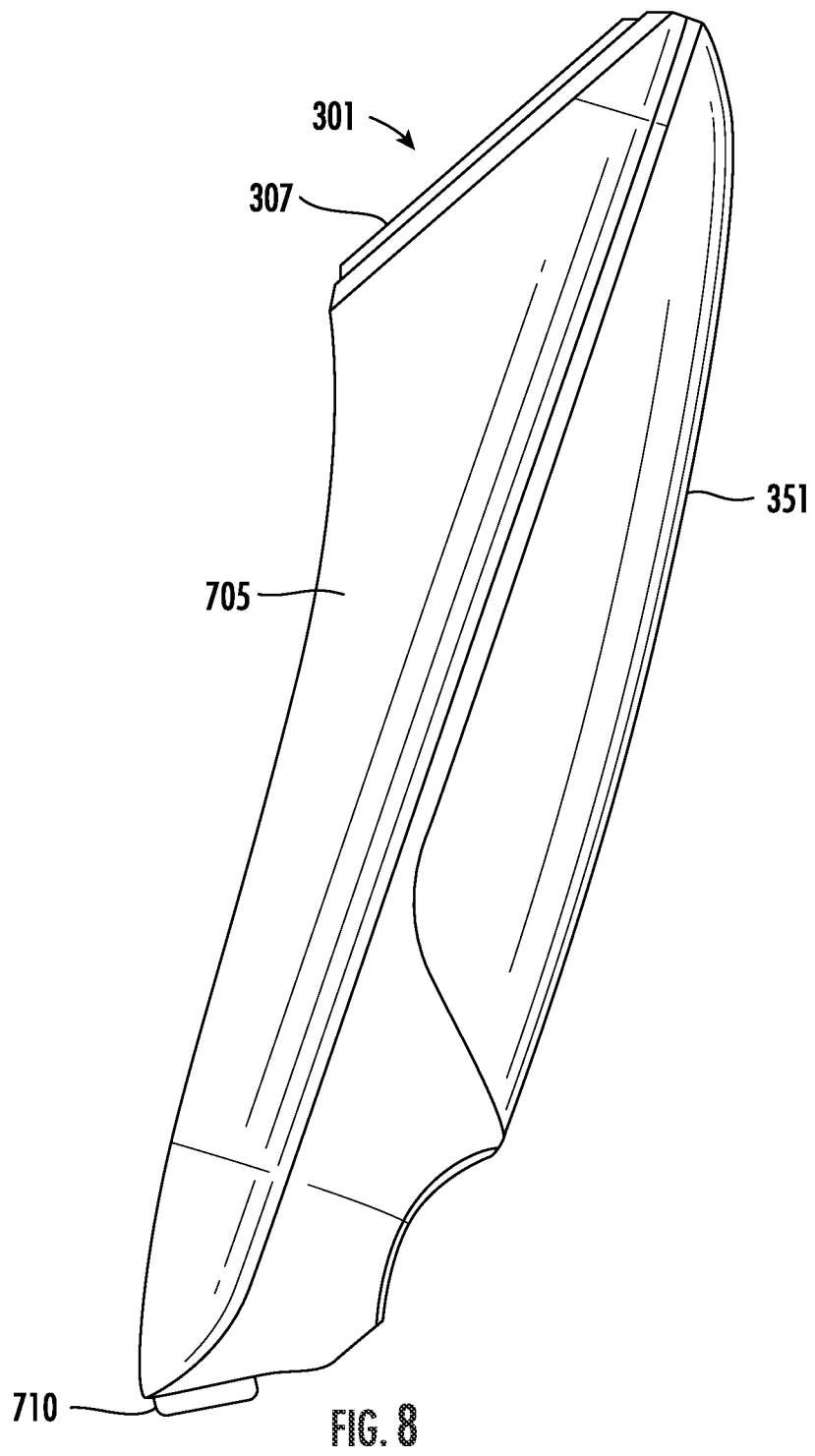
FIG. 8 shows a side view of the system unit.

FIG. 8 shows a side view system unit 301, in an implementation. The housing 705 of the system unit includes a bezel 710 that houses a portion of the probe tip. The bezel includes an opening the exposes a probe face of the probe tip.

Figure 9:
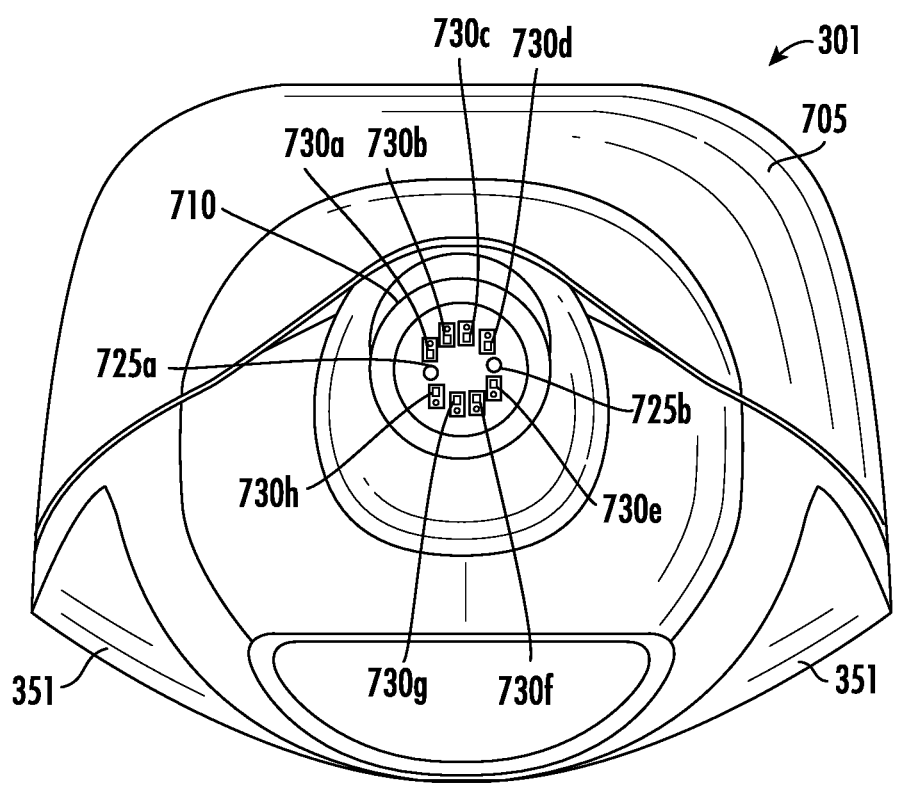
FIG. 9 shows an end view of the system unit.

FIG. 9 shows an end view of the second end of the system unit, in an implementation. The end of bezel 710 is shown with the probe face 715 in the opening of the bezel. The probe face may include an aperture plate 720 that includes a number of source apertures, for example, source apertures 725*a* and 725*b*, and includes a number of detector apertures 730*a*-730*h*. Each of the source apertures may be included in a source structure that may include light sources, such as one or more optical fibers, laser diodes, LEDs, one or more portions of the aperture plate, or other structures at the probe tip in any combination. Each of the detector apertures may be included in a detector structure that may include light detectors, such as one or more optical fibers, photodetectors, one or more portions of the aperture plate, or other structures at the probe tip in any combination.

Figure 10A:
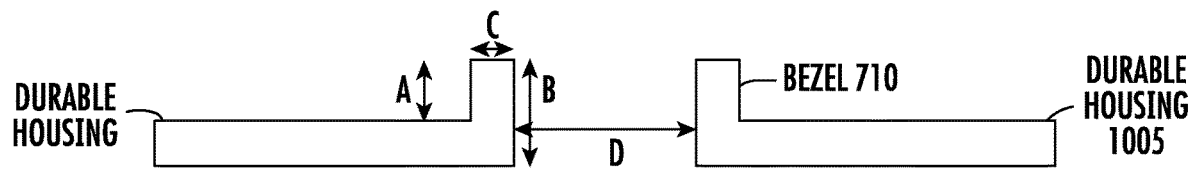
FIGS. 10A-10D show a number of steps for forming the probe face of the probe tip and forming the finished bezel of the housing of the system unit.

FIGS. 10A-10D show a number of steps for forming the probe face 715 of the probe tip 338 and forming the finished bezel 710 of the housing 1005 of the system unit 301. FIG. 10*a* shows the bezel 710 of the housing 1005 at an initial height A where the height is from the outside surface of the housing to the top of the bezel. Height A may be from about 3.5 millimeters to about 4 millimeters. In a specific implementation, height A is about 3.75 millimeters. The inner height B of the bezel is from the inside surface of the housing to the top of the bezel. Height B may be from about 4.5 millimeters to about 5.5 millimeters. In a specific implementation, height B is about 5.05 millimeters. The diameter D of the opening of the bezel may be from about 8 millimeters to about 10 millimeters. In a specific implementation, the diameter of the opening of the bezel may be about 9.1 millimeters. The width C of the bezel at the bezel's end may be about 1.0 millimeters to about 2.0 millimeters. The width C may vary around the circumference of the bezel. In a specific implementation, the width C of the bezel is about 1.5 millimeters.

Figure 10B:
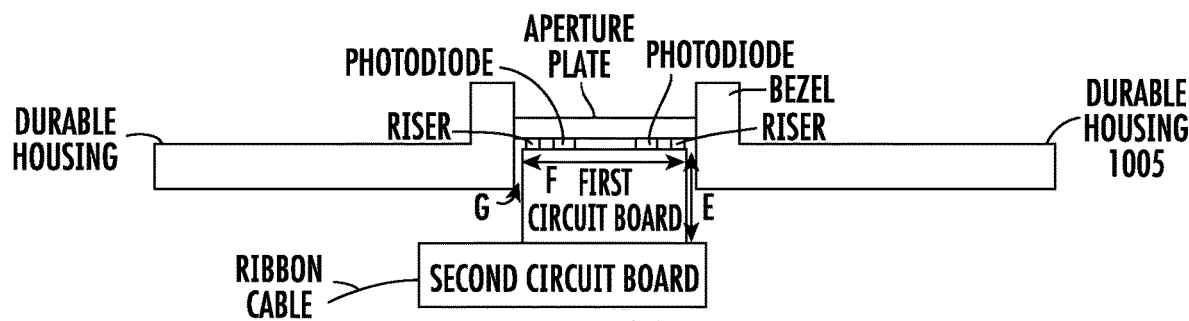

FIG. 10B shows the housing and bezel with a portion of the probe tip 338 in the housing and bezel. The portion of the probe tip shown includes a first circuit board 1020, a second circuit board 1025, riser 1030, photodiodes 1035, an aperture plate 1040, and a ribbon cable 1045 connected to the second circuit board. The first and second circuit boards may include electrical traces that are coupled. The second circuit board may be a fiberglass circuit board (e.g., FR4) that includes electrical traces that are connected to electrical traces of the first circuit board. The electrical traces of the first circuit board may extend upward from the second circuit board along the outer surface of the first circuit board. The first and second circuit boards may be connected by mechanical fasters, plastic welding, an adhesive (e.g., epoxy), another material, or any combination of these materials. The first circuit board may have a diameter F of about 6 millimeters to about 8 millimeters. In a specific implementation, the diameter F of the first circuit board is about 7 millimeters. The first circuit board may have a height E of about 3 millimeters to about 4 millimeters. In a specific implementation, the height E of the first circuit board is about 3.5 millimeters.

A distance G between the side of the first circuit board and the inner sidewall of the bezel may be about 0.5 millimeters to about 1.5 millimeters. In a specific embodiment, the distance between the side of the first circuit board and the inner sidewall of the bezel may be about 1.05 millimeters.

The riser may be connected to both the first circuit board and the aperture plate and may separate the first circuit board and aperture plate by a predetermined height. The photodiodes may be mounted on a top surface of the first circuit board and be connected to the electrical traces of the first circuit board. The aperture plate may include an aperture for each photodiode that is mounted on the first surface of the first circuit board and the diodes may respectively be inside the apertures. The height of each riser may be about 100 micrometers to about 200 micrometers. In an implementation, the height of each riser is about 150 micrometers.

Figure 10C:
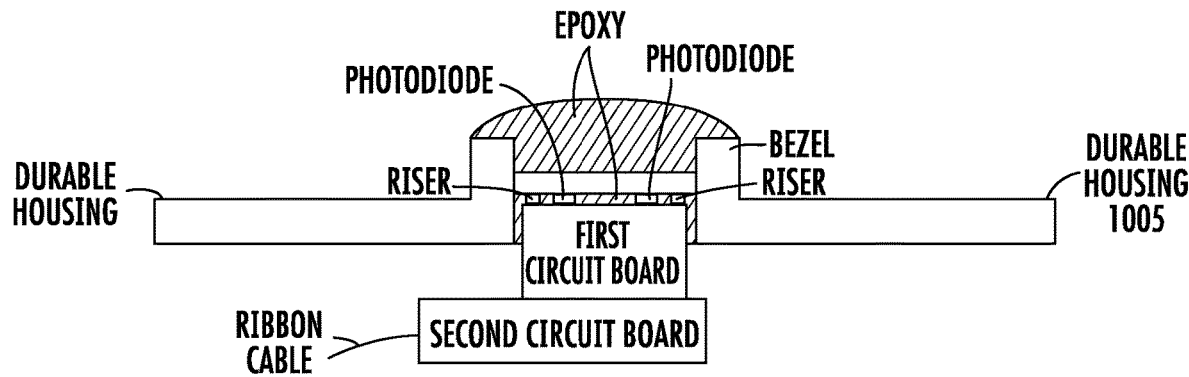

After the portion of the probe tip shown in FIG. 10B is placed into the opening of the bezel, epoxy is flowed into the opening as shown in FIG. 10C. The epoxy may flow into the apertures of the aperture plate, along the sides of the first circuit board, and may flow to the second circuit board and around the sides of the second circuit board.

Figure 10D:
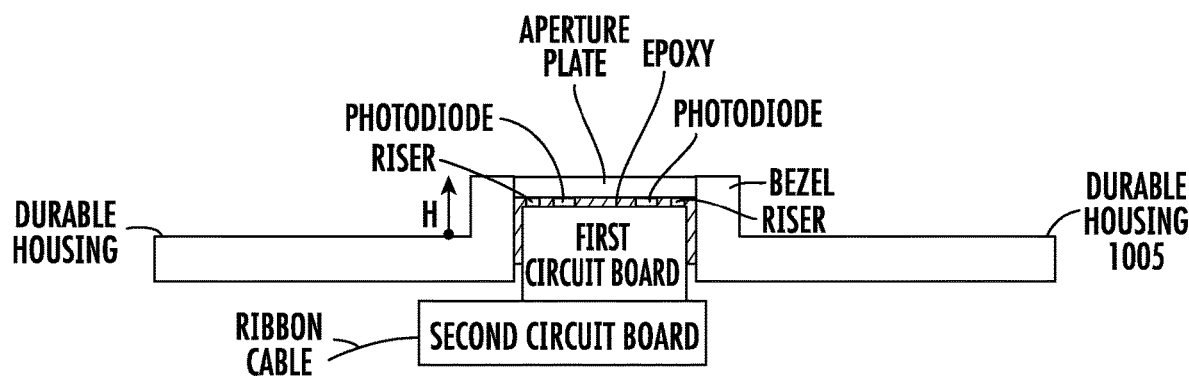

After the epoxy cures, the epoxy and a portion of the bezel may be removed (e.g., polished down) to a final height, as shown in FIG. 10D. The final outside height H of the bezel may be about 2.0 millimeters to about 3 millimeters. In a specific implementation, the final outside height H of the bezel is about 2.58 millimeters. In an implementation, a portion of the aperture plate may also be thinned (e.g., polished thinner) when the bezel and epoxy are removed. The aperture plate can include a marker embedded in the plate. The embedded marker is exposed and polished away in the polishing process, the polishing is completed when the marker is polished away.

In an implementation, the epoxy is polished down to the surface of the tops of the photodetectors inside the apertures of the aperture plate. In another implementation, a thin layer of epoxy remains over the tops of the photodiodes after polishing.

Figure 11:
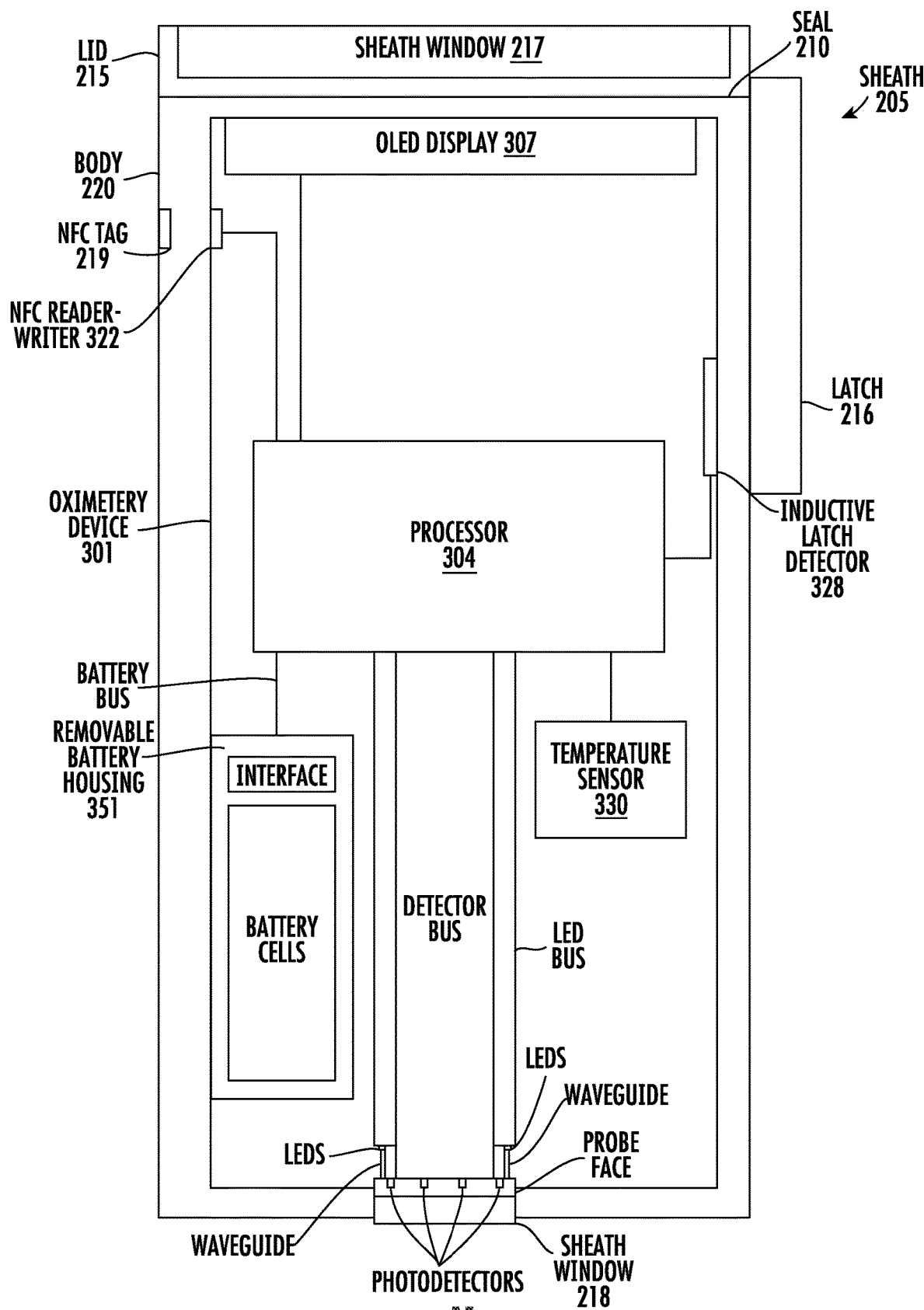
FIG. 11 is a block diagram of the system unit in a sheath, in an implementation.

FIG. 11 is an additional block diagram of system unit 301 in sheath 205, in an implementation. The sheath includes the seal 210, the lid 215, the body portion 220, a latch 216, a first sheath window 217, a second sheath window 218, and a radio-frequency communication device 219, such as an NFC (near-field communication) tag. The sheath may include a hinge that hinge couples the lid to the body portion and allows the lid to be opened and closed. Both the lid and sheath can be formed of a relatively rigid plastic material.

As described above, the latch latches that lid closed and seals the seal. The latch also releases the lid from the closed position and allows for the seal to be unsealed. The latch detector 328 (e.g., an inductor or a capacitive detector and an analog-to-digital converter (ADC) coupled to the processor) of the system unit is positioned nearest to the latch when the latch is closed (i.e., the first distance from the latch detector) so that the latch detector can detect when the latch is latched, the lid is closed, and the seal is sealed. That latch detector can detect when the latch opens and moves away from the first distance.

In an implementation, a first portion of the latch is rigidly connected to the lid and a second portion of the latch extends in a cantilever configuration from the lid. The first and second portions are opposite portions of the latch. The latch capable of bending to latch that latch to the body of the sheath and bending to unlatch the latch from the body. The latch can be steel, such as spring steel, which allows the second portion (e.g., cantilevered portion) of the latch to bend to latch and unlatch the latch from the body.

In an implementation, a first portion of the latch is rigidly connected to the body and the second portion of the latch extends in a cantilever configuration from the lid. The latch is capable of bending to latch that latch to the lid of the sheath and unlatch the latch from the lid.

The latch can be hinge connected to the lid via a lid hinge. With the lid hinge connected to the lid, that latch can rotate towards the body of the sheath and away from the body of the sheath to latch that latch to the body and unlatch the latch from the body. In another implementation, the latch is hinge connected to the body of the sheath and can rotate towards the lid and away from the lid to latch to the lid and unlatch from the lid.

In an implementation, the first window 217 is located in the lid of the sheath. The first window is positioned over the display 307 (e.g., an organic LED display) of the system unit when the lid of the sheath is closed. The first window can be transparent so that information displayed on the display is visible and discernable to a user when the lid of the sheath is closed. The first window can be a plastic material or glass. The first window can be sealed to the lid via an adhesive, such as epoxy, an O-ring, welding, heat-stake (if both materials are plastic), or another seal material. The seal can prevent contaminants (e.g., patient tissue, patient fluid, or other debris) from passing through the seal and contaminating the system unit. The sheath window may be a square-shaped window or a rectangular window that approximately matches the size and shape of display 307.

The second window 218 can be at an opposite end of the sheath from the first window. The second window can contact the probe face of the probe tip when the system unit is in the sheath. The second window can have a relatively flat surface that contacts the polished probe face so that relatively little air is trapped between the second widow and the probe face when the second window and probe face are in contact. In an implementation, the inside surface (e.g., inside the body of the sheath) of the second window can have an adhesive that can stick to the probe face of the system unit.

In an implementation, the NFC tag is coupled to an inner sidewall of the sheath. The inner sidewall that the NFC tag is coupled to may be an inner sidewall of the body of the sheath. The NFC tag may be coupled to the sidewall in a pocket formed on the sidewall, by an adhesive, a mechanical fastener, or any combination of these features. The NFC reader-writer may be inside an interior portion of the system unit. The NFC reader-writer may be coupled to an inner sidewall of the system unit by a pocket formed on the sidewall, by an adhesive, or both. In an embodiment, the NFC reader-writer is contained is a sticker that is adhered to an inside surface of the housing of the system unit. The NFC reader-write may be coupled to the printed circuit board that the processor in located on by a cable, such as a ribbon cable. The NFC tag and NFC reader-writer register with each other when the system unit is placed in the sheath so that the NFC tag and NFC reader-writer can communicate.

In an implementation, the I/O interface 322 of the system unit includes an NFC reader-writer. The NFC reader-writer can power the NFC tag 219 of the sheath so that the NFC reader-writer can communicate with the NFC tag. In some implementations, the NFC tag is battery powered by a battery of the NFC tag or of the sheath. In an implementation, the NFC tag is a read only NFC tag where information can be read from the NFC tag by the NFC reader-writer of the system unit. In an implementation, the NFC tag can be read and can be written to by the NFC reader-writer.

In an implementation, the NFC tag includes a memory (e.g., a nonvolatile memory, such as a FLASH memory or EEPROM, a nonvolatile memory, or both) that can store an identifier for the sheath, store an indicator that indicates whether the sheath has been previously used or is unused, other information, or any combination of this information. The identifier for the sheath can be an unencrypted identifier or an encrypted identifier that is previously stored in the memory. An identifier can be unique to a sheath or an identifier can be used for a number of sheaths. The identifier can identify the sheath as a particular type of sheath, such as a sheath that is reusable or a sheath that is not reusable. The identifier can be stored in the memory of the NFC tag by a manufacturer.

The NFC tag can include a number of other circuits, such as one or more of an antenna (a radio frequency (RF) antenna), an RF interface circuit (e.g., an analog-to-digital converter, a digital-to-analog converter, or both) that allows for the antenna to communicate with digital circuits in the NFC tag, an authentication circuit, a control circuit, an arithmetic logic unit, a cryptography circuit, a memory interface circuit, or other circuits. The NFC tag can include one or more of the circuits in any combination. The circuits can facilitate communication between the antenna and the memory device of the NFC tag of the sheath and with the NFC reader-writer of the system unit.

In an implementation, no metal is positioned between the NCF reader-write and the NFC tag. The distance between the NCF device is from about 10 millimeters to about 0.5 millimeters. In an implementation, the distance between the NCF device is from about 2.25 millimeters. The thickness of the housing of the system unit that is between the NFC device is from about 0.5 millimeters to about 3 millimeters. In an implementation, the thickness of the housing of the system unit that is between the NFC device is about 1.7 millimeters.

Figure 12:
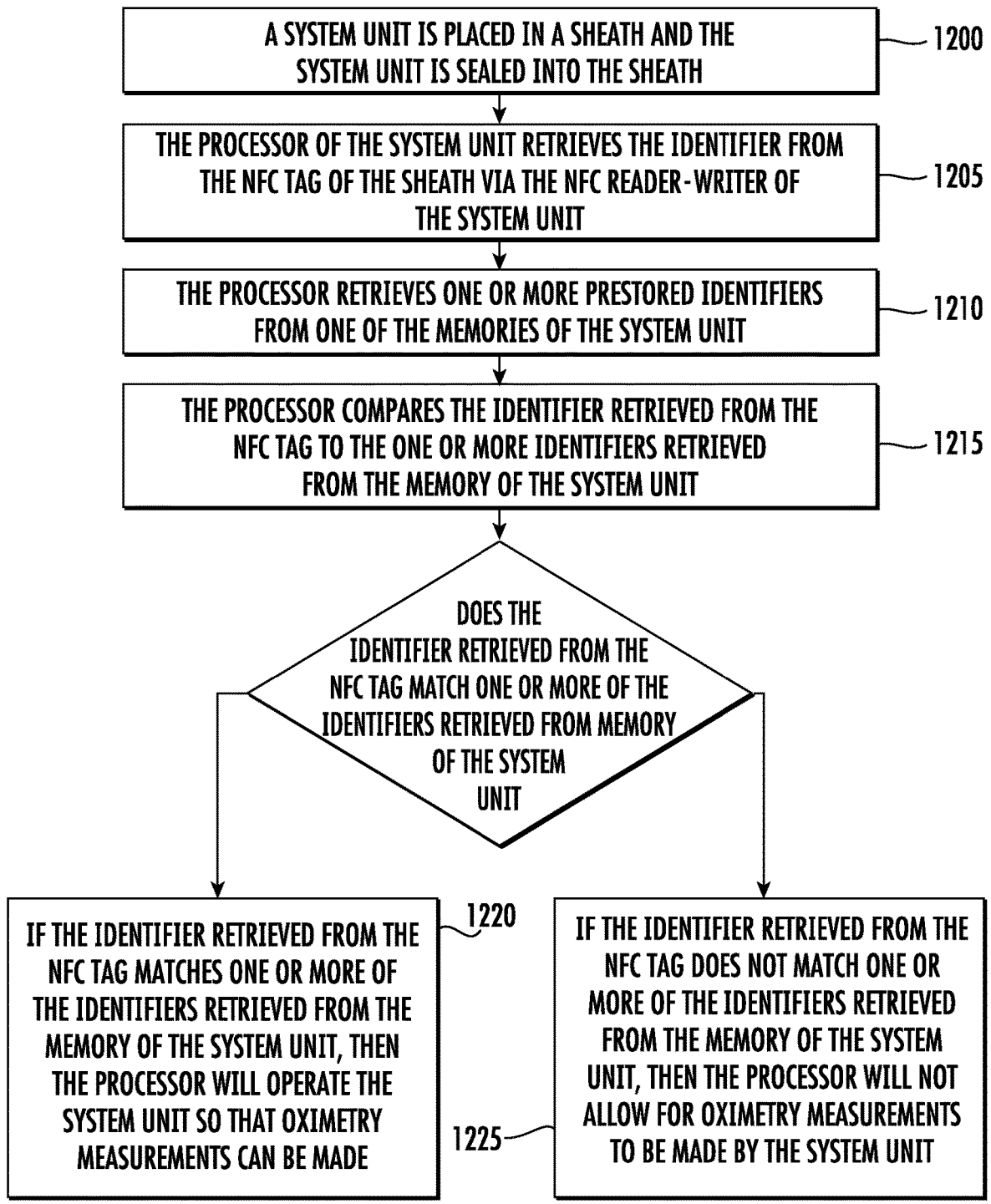
FIG. 12 is a flow diagram for a method of verifying whether an identifier stored in a sheath in which a system unit is placed in a valid identifier and whether the sheath is a valid sheath.

FIG. 12 is a flow diagram for a method of verifying whether an identifier stored in a sheath in which a system unit is placed, is a valid identifier and whether the sheath is a valid sheath. The flow diagram shows an example embodiment in an implementation. Steps may be added, removed, or combined without deviating from the method.

At 1200, a system unit is placed in a sheath and the system unit is sealed into the sheath by a user closing the lid and latching the sheath's latch.

At 1205, the processor of the system unit retrieves the identifier from the NFC tag of the sheath via the NFC reader-writer of the system unit according to an NFC communication protocol. More specifically, the NFC reader-writer can retrieve a string from the memory of the NFC tag. The string includes the identifier for the sheath and may include additional information. The additional information included in the string may include information that identifies whether the sheath has been previously used.

The retrieved string may be parsed by the processor or other circuit of the system unit to extract the identifier from the string, the previous use information, or both. If the identifier is encrypted, the processor or another decryption circuit of the system unit can decrypt the identifier.

At 1210, the processor retrieves one or more prestored identifiers from one of the memories (e.g., the nonvolatile memory) of the system unit.

In an embodiment, the one or more prestored identifiers are not stored in an encrypted form in the memory. In an embodiment, the one or more prestored identifiers are stored in an encrypted form in the memory. If the one or more identifiers are encrypted, the processor or another decryption circuit decrypts the one or more identifiers.

At 1215, the processor compares the identifier retrieved from the NFC tag to the one or more identifiers retrieved from the memory of the system unit to determine whether the identifier retrieved from the NFC tag matches one or more of the identifiers retrieved from the memory of the system unit. In an embodiment, one integrated circuit (e.g., the processor) performs the decryption of the one or more prestored identifiers, the identifier retrieved from the NFC tag, or both, and compares the one or more prestored identifiers with the identifier retrieved from the NFC tag without transmitting the decrypted identifiers out of the integrated circuit. Therefore a dishonest actor will be inhibited from accessing the decrypted identifiers.

At 1220, if the identifier retrieved from the NFC tag matches one or more of the identifiers retrieved from the memory of the system unit, then the processor will operate the system unit so that oximetry measurements can be made (e.g., a normal mode of operation). The processor can operate the system unit with or without displaying information on the display that indicates the authenticity of the sheath. The identifier retrieved from the NFC tag may also be used by the system unit to affect one or more operations of the system unit, such as being used for process control flow of a method of operation of the system unit. For example, the state of an NFC tag may be used by the system unit for branch logic decisions in a method of operation, skipping one or more steps in a method of operation of the system unit, or may be used for decision making for other workflow steps.

At 1225, if the identifier retrieved from the NFC tag does not match one or more of the identifiers retrieved from the memory of the system unit, then the processor will not operate the system unit and will not allow for oximetry measurements to be made by the system unit. The processor may cause a message to be displayed on the display indicating that the system unit will not operate with the sheath, indicate that the sheath is an unauthenticated sheath, other messages, or any combination of these messages.

Figure 13:
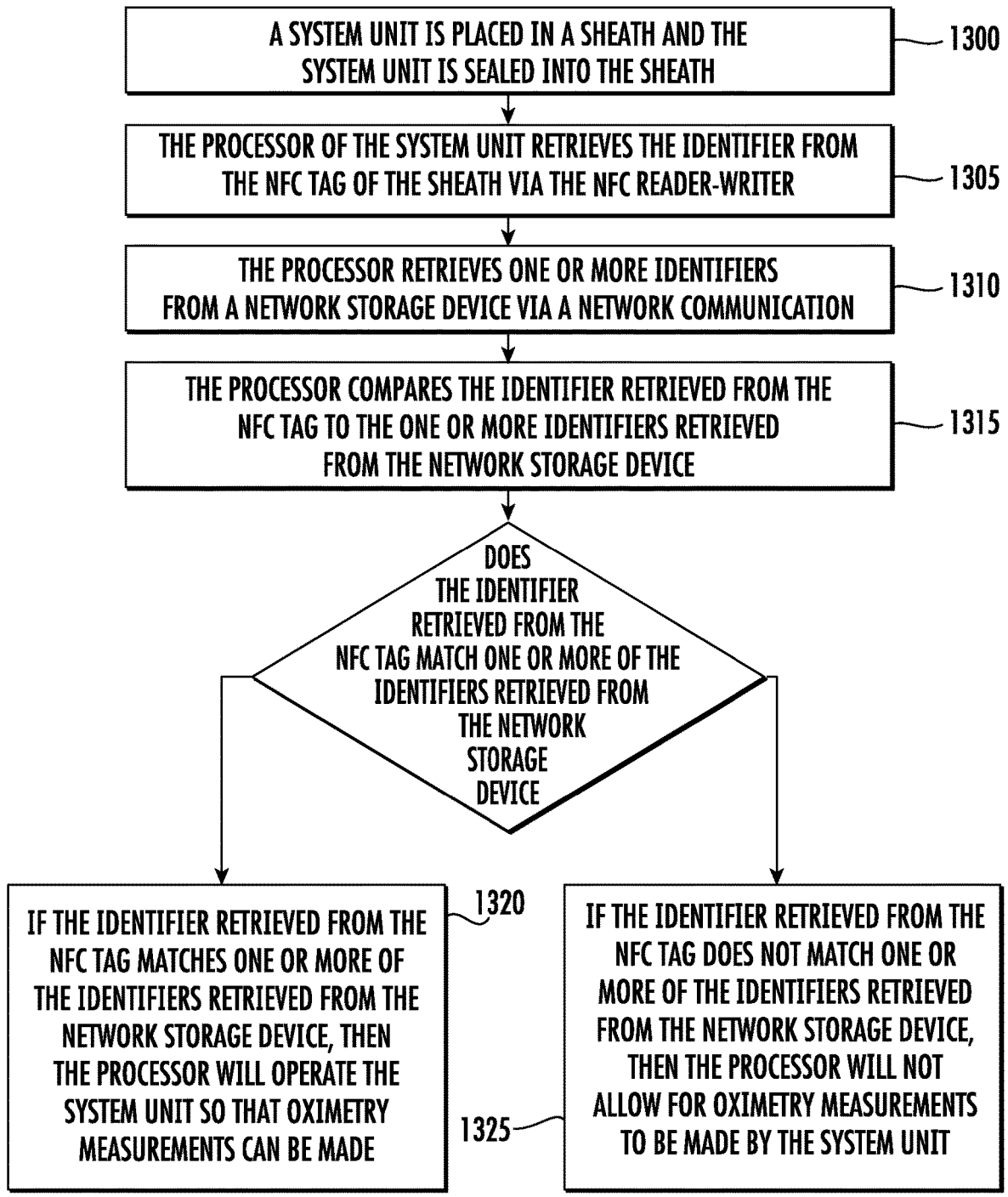
FIG. 13 is a flow diagram for a method of verifying whether an identifier stored in a sheath in which a system unit is placed in a valid identifier and whether the sheath is a valid sheath.

FIG. 13 is a flow diagram for a method of verifying whether an identifier stored in a sheath in which a system unit is placed, is a valid identifier and whether the sheath is a valid sheath. The flow diagram shows an example embodiment in an implementation. Steps may be added, removed, or combined without deviating from the method.

At 1300, a system unit is placed in a sheath and the system unit is sealed into the sheath by a user closing the lid and latching the sheath's latch.

At 1305, the processor of the system unit retrieves the identifier from the NFC tag of the sheath via the NFC reader-writer of the system unit according to an NFC communication protocol. More specifically, the NFC reader-writer can retrieve a string from the memory of the NFC tag. The string includes the identifier for the sheath and may include additional information. The additional information included in the string may include information that identifies whether the sheath has been previously used.

The retrieved string may be parsed by the processor or other circuit of the system unit to extract the identifier from the string, the previous use information, or both. If the identifier is encrypted, the processor or another decryption circuit of the system unit can decrypt the identifier.

At 1310, the processor retrieves one or more identifiers from a storage device that is detached from the system unit. For example, the processor of the system unit can retrieve one or more identifiers from a network storage device via a network communication where the network interface 326 communicates with a remote server via a network (e.g., the Internet, an intranet, other network structures, or any combination of the structures) to retrieve the one or more identifiers. If the one or more identifiers are encrypted, the processor or another decryption circuit can decrypt the one or more identifiers.

At 1315, the processor compares the identifier retrieved from the NFC tag to the one or more identifiers retrieved from the network storage device to determine whether the identifier retrieved from the NFC tag matches one or more of the identifiers retrieved from the network.

At 1320, if the identifier retrieved from the NFC tag matches one or more of the identifiers retrieved from the network storage device, then the processor will operate the system unit so that oximetry measurements can be made (e.g., a normal mode of operation). The processor can operate the system unit with or without displaying information on the display that indicates the authenticity of the sheath.

At 1325, if the identifier retrieved from the NFC tag does not match one or more of the identifiers retrieved from the network storage device, then the processor will not operate the system unit and will not allow for oximetry measurements to be made by the system unit. The processor may cause a message to be displayed on the display indicating that the system unit will not operate with the sheath, indicate that the sheath is an unauthenticated sheath, other messages, or any combination of these messages.

Figure 14:
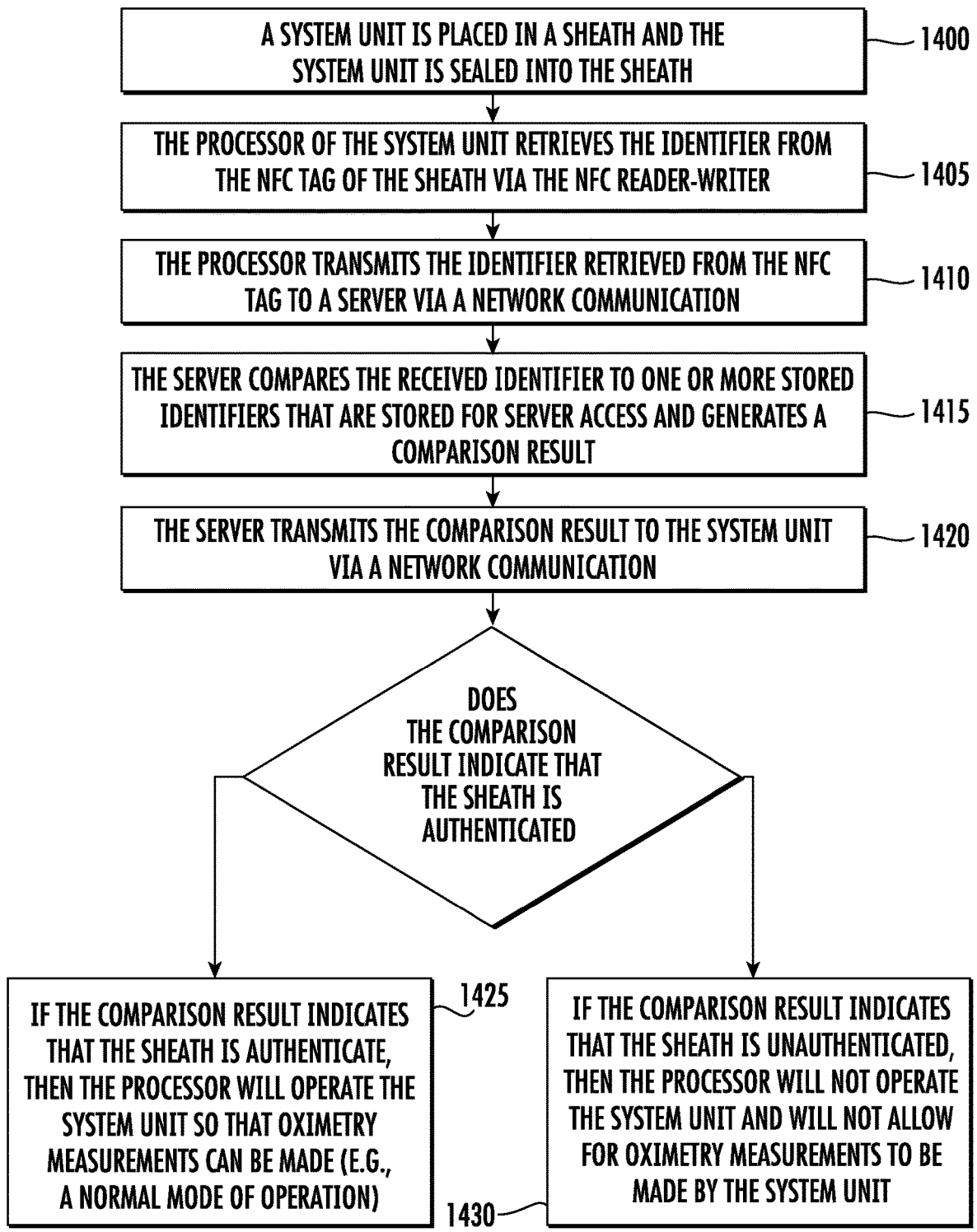
FIG. 14 is a flow diagram for a method of verifying whether an identifier stored in a sheath in which a system unit is placed in a valid identifier and whether the sheath is a valid sheath.

FIG. 14 is a flow diagram for a method of verifying whether an identifier stored in a sheath in which a system unit is placed, is a valid identifier and whether the sheath is a valid sheath. The flow diagram shows an example embodiment in an implementation. Steps may be added, removed, or combined without deviating from the method.

At 1400, a system unit is placed in a sheath and the system unit is sealed into the sheath by a user closing the lid and latching the sheath's latch.

At 1405, the processor of the system unit retrieves the identifier from the NFC tag of the sheath via the NFC reader-writer of the system unit according to an NFC communication protocol. More specifically, the NFC reader-writer can retrieve a string from the memory of the NFC tag. The string includes the identifier for the sheath and may include additional information. The additional information included in the string may include information that identifies whether the sheath has been previously used.

The retrieved string may be parsed by the processor or other circuit of the system unit to extract the identifier from the string, the previous use information, or both. If the identifier is encrypted, the processor or another decryption circuit of the system unit can decrypt the identifier.

At 1410, the processor transmits the identifier retrieved from the NFC tag to a server via a network communication. For example, the processor of the system unit can transmit the identifier to a server via the network interface 326 where the network interface communicates with the server via a network (e.g., the Internet, an intranet, other network structures, or any combination of the structures).

At 1415, the server compares the received identifier to one or more stored identifiers that are stored for server access and generates a comparison result. The comparison result can indicate that the sheath is an authenticated sheath, for example, if the identifier stored in the NFC tag matches one or more of the identifiers that the server can access. Alternatively, the comparison result can indicate that the sheath is an unauthenticated sheath, for example, if the identifier stored in the NFC tag does not match one or more of the identifiers that the server can access.

At 1420, the server transmits the comparison result to the system unit via a network communication.

At 1425, if the comparison result indicates that the sheath is authenticated, then the processor will operate the system unit so that oximetry measurements can be made (e.g., a normal mode of operation). The processor can operate the system unit without displaying information on the display that indicates the authenticity of the sheath.

At 1430, if the comparison result indicates that the sheath is unauthenticated, then the processor will not operate the system unit and will not allow for oximetry measurements to be made by the system unit. The processor may cause a message to be displayed on the display indicating that the system unit will not operate with the sheath, indicate that the sheath is an unauthenticated sheath, other messages, or any combination of these messages.

Figure 15:
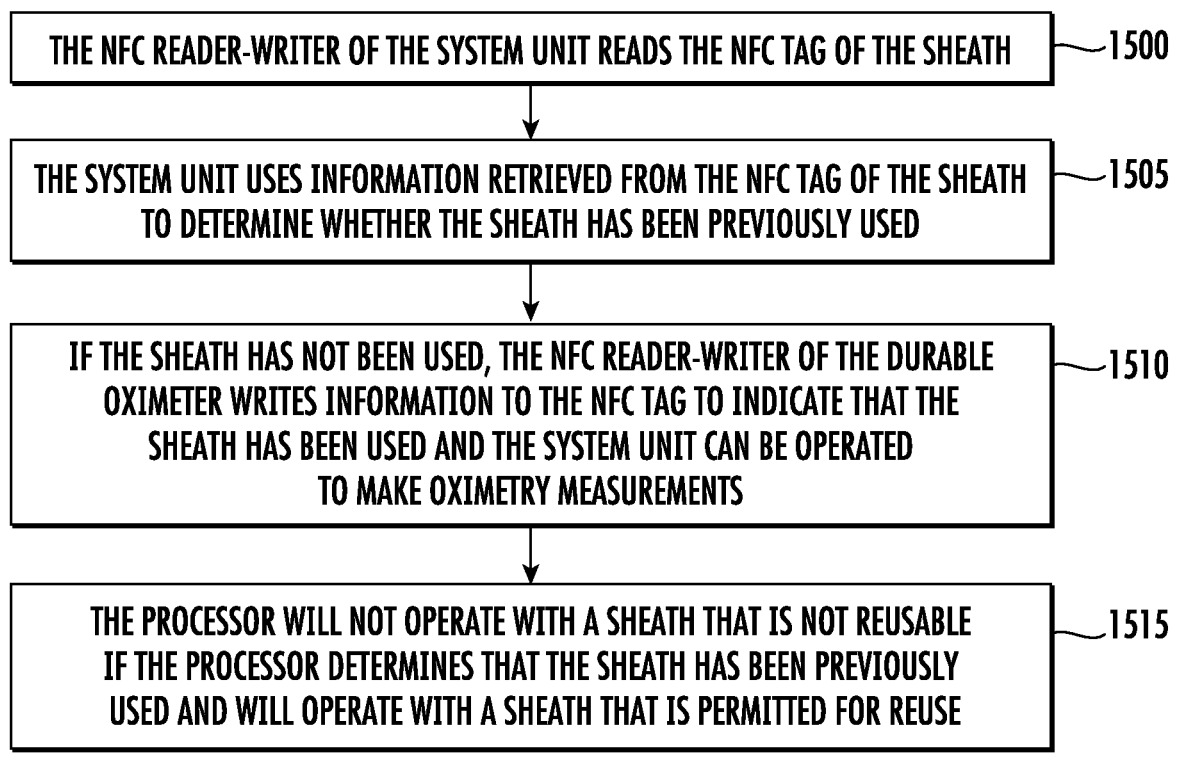
FIG. 15 is a flow diagram for a method of verifying whether an identifier stored in a sheath indicates whether the sheath has been previously used.

FIG. 15 is a flow diagram for a method of verifying whether an identifier stored in a sheath indicates whether the sheath has been previously used. The flow diagram shows an example embodiment in an implementation. Steps may be added, removed, or combined without deviating from the method.

At 1500, the NFC reader-writer of the system unit reads the NFC tag of the sheath to determine whether information is stored in the NFC tag indicating that the sheath has previously been used. The information can be a number. The information can be a single bit that is set to 1 or 0 to indicate that the sheath has or has not been previously used. The information can be another identifier that may be encrypted or decrypted. If the identifier is encrypted, the processor or another circuit (e.g., a decryption circuit) can decrypt the identifier.

At 1505, the system unit uses the information retrieved from the NFC tag of the sheath to determine whether the sheath has been previously used. For example, if the information is a number that indicates a number of uses of the sheath and the number is nonzero, then the number indicates that the sheath has been previously used. The use information for the sheath may be encrypted. If the use information is encrypted, the processor or another circuit in the system unit may decrypt the use information.

At 1510, if the sheath has not been used, the NFC reader-writer of the durable oximeter writes information (e.g., stores a use bit) to the NFC tag to indicate that the sheath has been used.

At 1515, the processor will not operate with a sheath that is not reusable if the processor determined that the sheath has been previously used, but will operate with a sheath that is permitted for reuse. If the processor determines that the system unit has been previously used, an error message may be displayed on the display of the system unit. The error message may indicate the nature of the error (e.g., prior use of the sheath), that the error is unrecoverable, that a new sheath may be coupled to the system unit for use, another message, or any combination of these messages.

Figure 16:
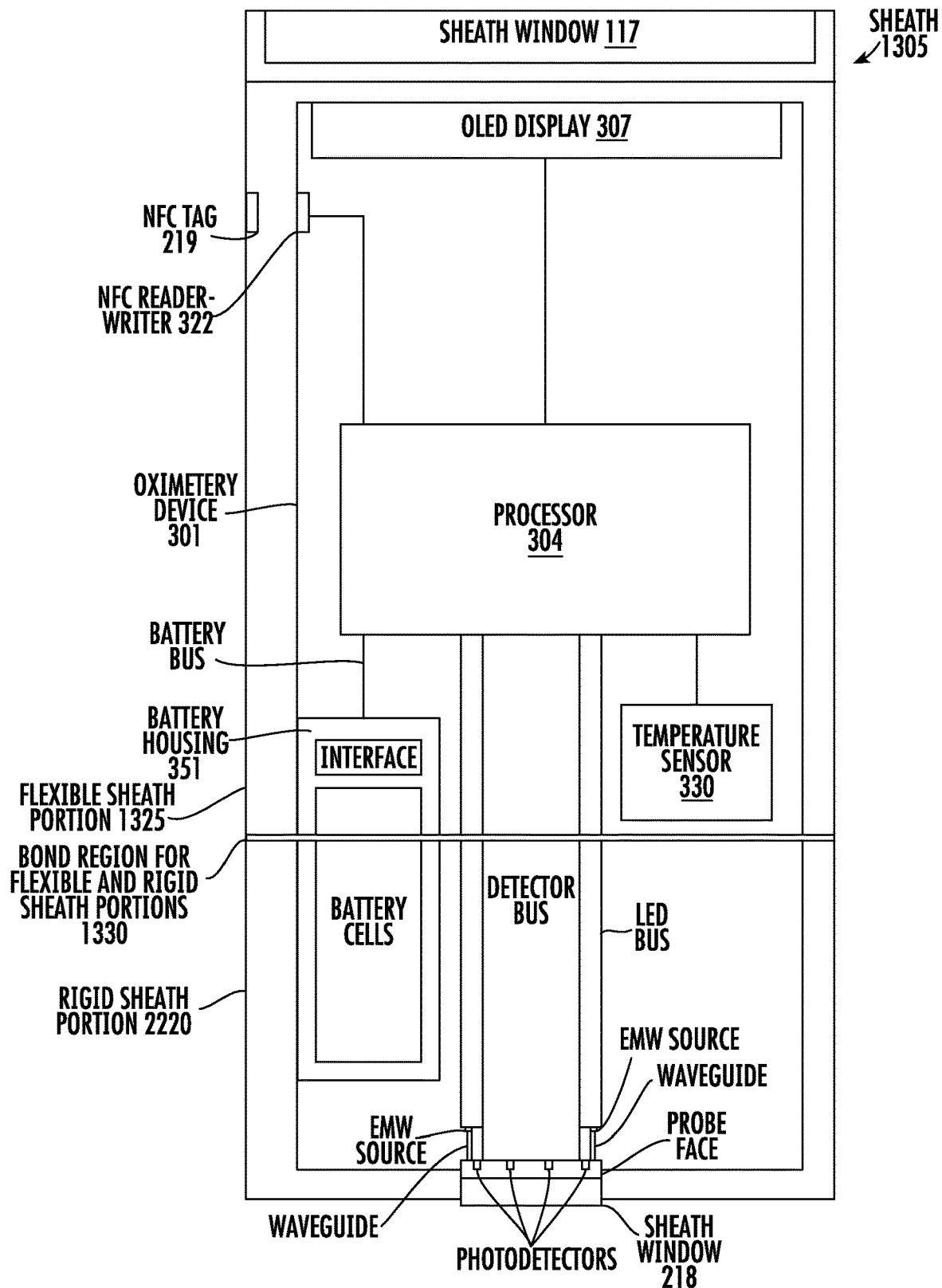
FIG. 16 is a block diagram of system unit 301 in sheath 1305, in an implementation.

FIG. 16 is a block diagram of system unit 301 in sheath 1305, in an implementation. Sheath 1205 is similar to sheath 205 but differs in that a lower body portion 1320 of the sheath is a relatively rigid plastic material and an upper body portion 1325 of the sheath is a relatively flexible plastic material. That is, the material of the upper body portion has a higher flexibility than the lower body portion. The upper and lower body portions may be coupled by an adhesive 1330, sonic welding, or another bonding material that forms a seal between the body portions. The seal is a barrier to patient tissue, patient liquid, and other contaminants. A top portion of the upper body portion can be seal so that a system unit can be sealed in the sheath where patient tissue, patient liquid, and other contaminants cannot reach the system unit when the unit is sealed in the sheath.

Figure 17:
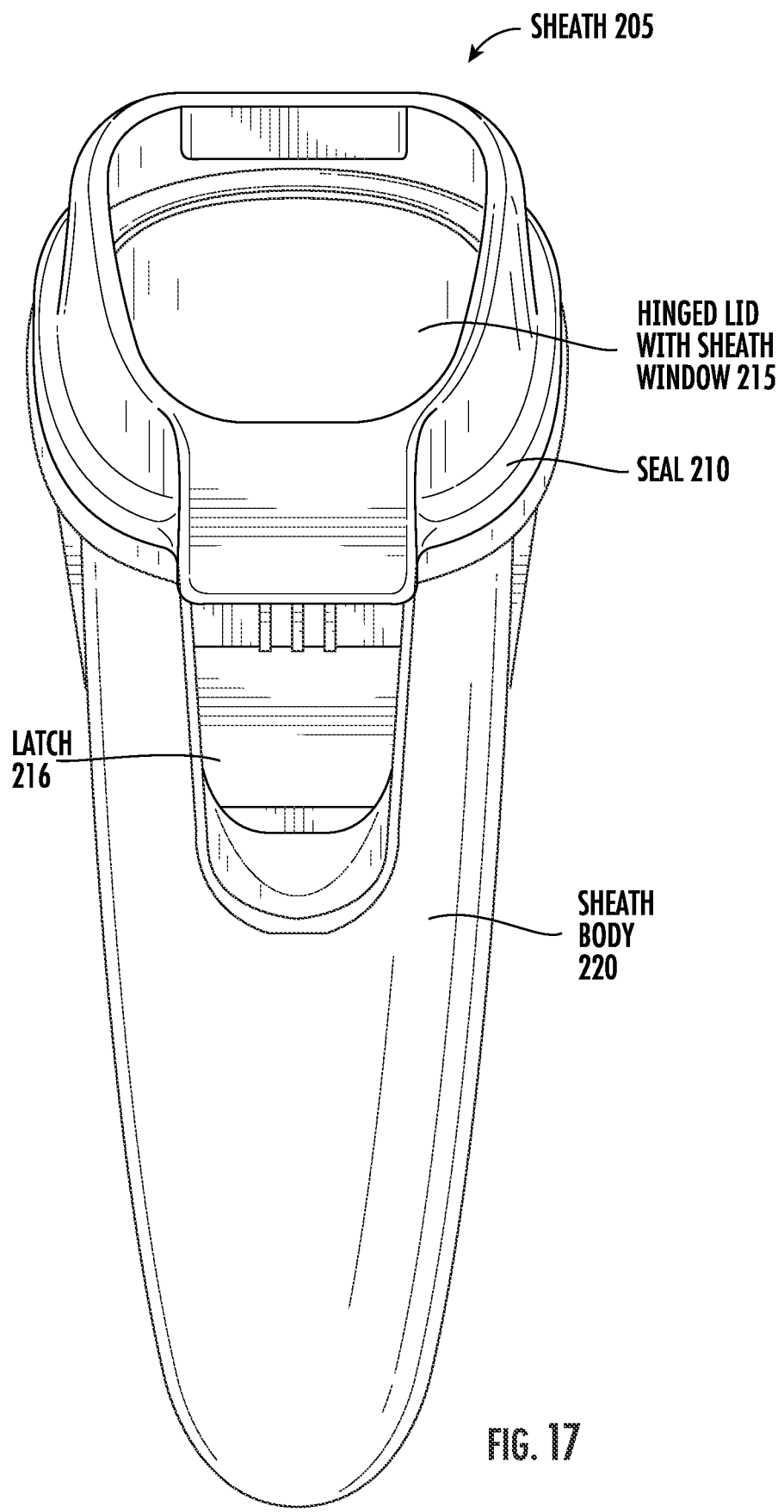
FIG. 17 shows a front view of the sheath, in an implementation.

FIG. 17 shows a front view of the sheath 205, in an implementation. The sheath is shown in FIG. 17 with the lid 215 closed against the body 220 of the sheath with the latch in a latched position against the body. The lid may be formed of a first plastic material that can be transparent (e.g., the window of the lid), translucent (e.g., portions of the lid attached to the window), opaque, or any combination of these properties. The body may be formed of a second plastic that can be transparent, translucent, opaque, or any combination of these properties. The second window of the body may be attached to the body via an adhesive (e.g., epoxy), plastic weld, or other fasteners. The second widow may form a seal with the body where the second window attaches to the body where contaminants cannot pass through the seal to contaminate a system unit in the sheath via the seal.

In an implementation, the lid of the sheath is a plastic material. The material can be polycarbonate, acrylic, polyethylene terephthalate (PET), PETG, polyester, acrylonitrile butadiene styrene (ABS), or other plastic material. Polycarbonate, for example, is a material the lid may be made of because the material is easy to form, transparent, and can be sterilized by a variety of sterilization techniques and material, such as ethylene oxide (EtO), exposed to irradiation (both gamma and electron-beam), and steam autoclaving, isopropyl alcohol exposure, and other techniques and materials.

The body of the sheath is a plastic material. The material can be polycarbonate, acrylic, polyethylene terephthalate (PET), PETG, polyester, acrylonitrile butadiene styrene (ABS), or other plastic material. ABS, for example, is a material the body may be made of because the material is easy to form and can be sterilized by a variety of sterilization techniques and material, such as ethylene oxide (EtO), exposed to irradiation (both gamma and electron-beam), and steam autoclaving, isopropyl alcohol exposure, and other techniques and materials.

The second window of the sheath at the bottom of the sheath is a plastic material or a glass material. In an implementation, the window is a plastic material. The material can be polycarbonate, acrylic, polyethylene terephthalate (PET), PETG, clear polyester, clear acrylonitrile butadiene styrene (ABS), or other transparent plastic material. PET, for example, is a material the second window may be made of because the material is easy to form, can be made optically flat, can be transparent, can be relatively strong while relatively thin, and can be sterilized by a variety of sterilization techniques and material, such as ethylene oxide (EtO), exposed to irradiation (both gamma and electron-beam), and steam autoclaving, isopropyl alcohol exposure, and other techniques and materials. The glass can be silica, borosilicate glass, optical glass, or other types of glass, such as other types of hard glass.

Figure 18:
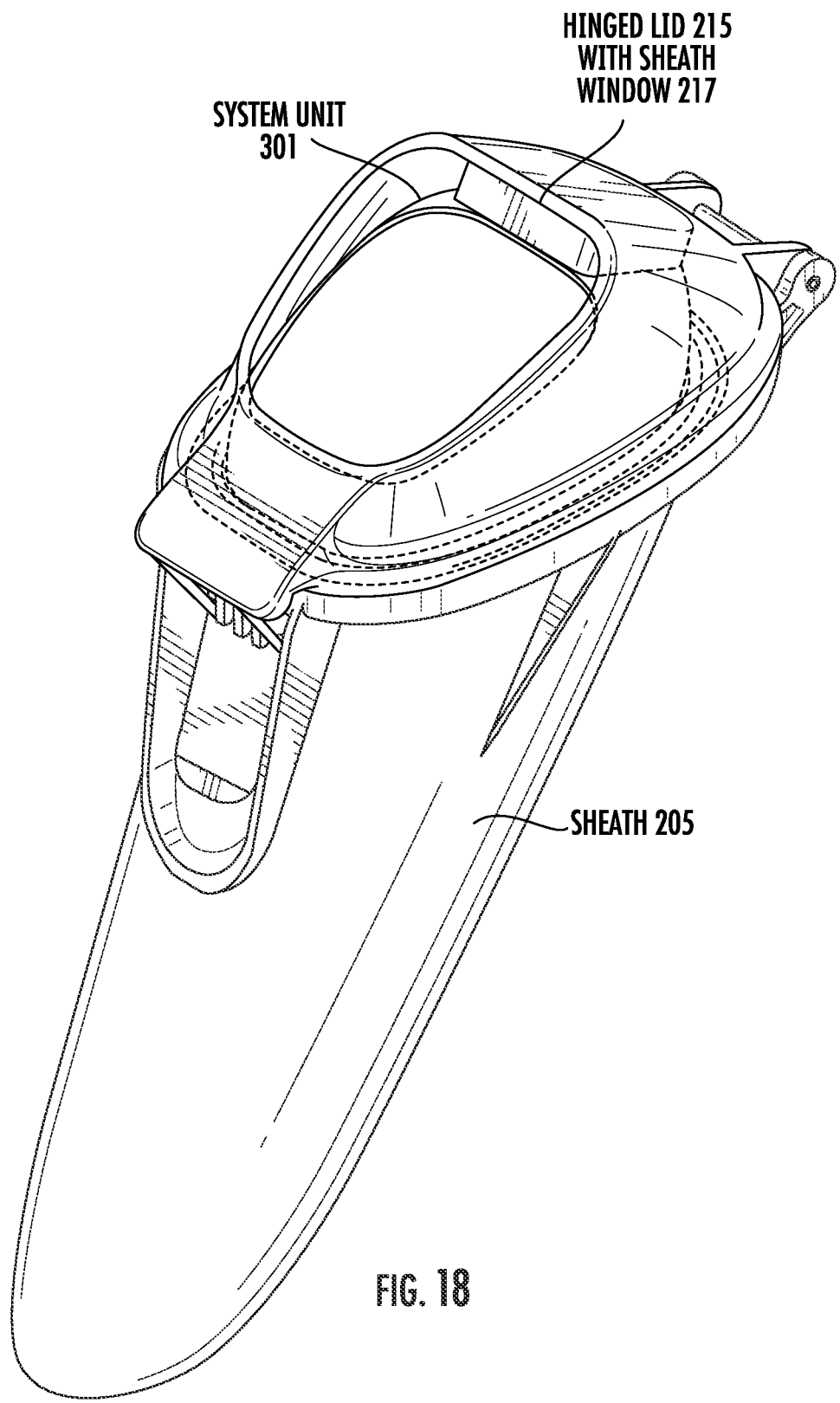
FIG. 18 shows a perspective view of the sheath and the system unit in the sheath, in an implementation.

FIG. 18 shows a perspective view of the sheath, system unit, and battery pack, in an implementation. The sheath is shown with the sheath lid closed and the system unit with the battery pack attached is in the sheath. The display of the system unit is visible through the first window of the lid of the sheath. Information (e.g., text, graphics, or both) that is displayed on the display of the system unit is visible to a user looking through the second window of the lid. The display and window are both proximally located with the probe face and second window distally located when the system is ready for use. With the second window in contact with tissue, the display faces away from the tissue so that the display, through the first window, can be seen by a user.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method comprising:
   retrieving, when an oximeter device is located in a sheath, encrypted information by a first radio frequency (RF) communication device of the oximeter device from a second RF communication device of the sheath using an RF communication, wherein the oximeter device comprises:
   a top housing comprising a display visible from an exterior of the top housing; and
   a bottom housing comprising a printed circuit board, a processor formed on the printed circuit board, a probe tip coupled to the processor, and a first wall, wherein the first wall comprises a front side surface, a backside surface, and an opening extending from the front side surface to the backside surface, the printed circuit board is coupled to the front side surface of the first wall,
   the printed circuit board comprises a near field read-writer, a plurality of electrical contacts located on the backside surface and coupled to the processor,
   the electrical contacts on the backside surface of the printed circuit board are visible through the opening formed in the first wall of the bottom housing,
   the backside surface of the first wall comprises a first riser that extends from the backside surface of the first wall, the first riser comprises a sidewall, an angle between at least a portion of the sidewall of the first riser and the backside surface of the first wall is less than a straight angle;
   decrypting, by a decryption circuit of the oximeter device, the encrypted information to produce a first identifier code for the sheath;
   retrieving a second identifier code for the sheath from a memory of the oximeter device;
   comparing the first and second identifier codes to determine if the first and second identifier codes are the same code;
   if the first and second identifier codes match based on the comparison, enabling the oximeter device to make oximetry measurements of tissue; and
   if the first and second identifier codes do not match, not enabling the oximeter device to make oximetry measurements of tissue and displaying a message on the display of the oximeter device that the oximetry device is not operable with the sheath.

2. The method of claim 1 comprising decrypting, by the decryption circuit of the oximeter device, the second identifier code.

3. The method of claim 2 comprising performing the comparing of the first and second identifier codes by the decryption circuit; and not transmitting the first and second identifier codes out from the decryption circuit.

4. The method of claim 3 wherein the decryption circuit is a second processor of the oximeter device.

5. The method of claim 1 wherein the second identifier code is prestored in the memory of the oximeter device.

6. The method of claim 1 wherein the first radio frequency communication device is a first near field communication (NFC) device and the second radio frequency communication device is a second NFC device.

7. The method of claim 1 wherein the decrypting, by the decryption circuit of the oximeter device, the encrypted information produces first use information of the sheath; and the method comprising determining by the oximeter device if the sheath has been previously used based on the first use information; enabling the oximeter device to make oximetry measurements of tissue if the sheath has not been previously used; and disabling the oximeter device from making oximetry measurements of tissue if the sheath has been previously used and displaying the message on the display of the oximeter device that indicates that the oximetry device is not operable with the sheath.

8. The method of claim 7 comprising transmitting second use information from the first NFC device of the oximeter device to the second NFC device of the sheath; storing the second use information in a memory of the second NFC device, wherein the second use information is an indicator that the sheath has been used.

9. The method of claim 8 wherein the second use information is encrypted use information and is stored in encrypted form in the second NFC device of the sheath.

10. The method of claim 3 wherein the decryption circuit is the processor of the oximeter device.

11. The method of claim 3 comprising allowing for the second RF communication to be located inside an interior space of the sheath.

12. The method of claim 11 comprising allowing for the oximeter device to be located inside the interior space of the sheath.

13. The method of claim 12 comprising allowing for the oximeter device to be sealed inside the interior space of the sheath when a first opening of the top housing of the sheath and a second opening of the bottom housing of the sheath are sealed together.

14. The method of claim 11 comprising allowing the top and bottom housings of the sheath to be coupled by a hinge, wherein the top and bottom housing can rotate with respect to each other via the hinge to form the interior space.

15. A method comprising:
   retrieving, when an oximeter device is located in a sheath, encrypted information by a first radio frequency (RF) communication device of the oximeter device from a second RF communication device of the sheath using an RF communication;
   decrypting, by a decryption circuit of the oximeter device, the encrypted information to produce a first identifier code for the sheath;
   retrieving a second identifier code for the sheath by the oximeter device from a server;
   comparing the first and second identifier codes to determine if the first and second identifier codes are the same code;
   if the first and second identifier codes match based on the comparison, enabling the oximeter device to make oximetry measurements of tissue; and
   if the first and second identifier codes do not match, not enabling the oximeter device to make oximetry measurements of tissue and displaying a message on a display of the oximeter device that the oximetry device is not operable with the sheath.

16. The method of claim 15 comprising decrypting, by the decryption circuit of the oximeter device, the second identifier code retrieved from the server.

17. The method of claim 16 comprising performing the comparing of the first and second identifier codes by the decryption circuit; and not transmitting the first and second identifier codes out from the decryption circuit.

18. The method of claim 17 wherein the decryption circuit is a processor of the oximeter device.

19. The method of claim 15 wherein the first radio frequency communication device is a first near field communication (NFC) device and the second radio frequency communication device is a second NFC device.

20. The method of claim 15 wherein the decrypting, by a decryption circuit of the oximeter device, the encrypted information produces first use information of the sheath; and the method comprising determining by the oximeter device if the sheath has been previously used based on the first use information; enabling the oximeter device to make oximetry measurements of tissue if the sheath has not been previously used; and disabling the oximeter device from making oximetry measurements of tissue if the sheath has been previously used and displaying the message on the display of the oximeter device that indicates that the oximetry device is not operable with the sheath.

21. The method of claim 20 comprising transmitting second use information from the first NFC device of the oximeter device to the second NFC device of the sheath; storing the second use information in a memory of the second NFC device, wherein the second use information is an indicator that the sheath has been used and is stored in encrypted form in the second NFC device of the sheath.

22. A method comprising:
retrieving, when an oximeter device is located in a sheath, encrypted information by a first radio frequency (RF) communication device of the oximeter device from a second RF communication device of the sheath using an RF communication;
transmitting the encrypted information to a server;
decrypting, by the server, the encrypted information to produce a first identifier code for the sheath;
retrieving, by the server, a second identifier code for the sheath from a database;
comparing the first and second identifier codes to determine if the first and second identifier codes are the same code;
if the first and second identifier codes match based on the comparison, transmitting first authentication information to the oximetry device, wherein the first authentication information indicates that the sheath is authenticated;
enabling the oximeter device to make oximetry measurements of tissue if the sheath is authenticated;
if the first and second identifier codes do not match based on the comparison, transmitting second authentication information to the oximetry device, wherein the second authentication information indicates that the sheath is not authenticated; and
not enabling the oximeter device to make oximetry measurements of tissue if the sheath is not authenticated and displaying a message on a display of the oximeter device that the oximetry device is not operable with the sheath.

23. The method of claim 22 comprising decrypting, by the server, the second identifier code retrieved from the database.

24. The method of claim 22 wherein the decrypting by the server comprises producing first use information of the sheath; and the method comprising: determining by the server if the sheath has been previously used based on the first use information;
if the sheath has not previously been used, transmitting third authentication information to the oximetry device, wherein the third authentication information indicates that the sheath has not previously been used;
enabling the oximeter device to make oximetry measurements of tissue if the sheath has not previously been used; and
if the sheath has previously been used, transmitting fourth authentication information to the oximetry device, wherein the fourth authentication information indicates that the sheath has previously been used and not enabling the oximeter device to make oximetry measurements of tissue if the sheath has previously been used.

25. The method of claim 22 comprising transmitting second use information from the first NFC device reader writer of the oximeter device to the second NFC device of the sheath; storing the second use information in a memory of the second NFC device in encrypted form, wherein the second use information is an indicator that the sheath has been used.

* * * * *